United States Patent
Willard et al.

(10) Patent No.: US 10,940,247 B2
(45) Date of Patent: *Mar. 9, 2021

(54) COLLECTION JAR AND COLLECTION BASKET FOR SURGICAL USE

(71) Applicant: Tobra Medical, Inc., Wake Forest, NC (US)

(72) Inventors: Gretchen Willard, Durham, NC (US); Eli Breeden Nichols, Durham, NC (US); Thomas Ralph Blackburn, III, Fuquay-Varina, NC (US); Theodore J. Mosler, Raleigh, NC (US)

(73) Assignee: Tobra Medical, Inc., Wake Forest, NC (US)

( * ) Notice: Subject to any disclaimer, the term of this patent is extended or adjusted under 35 U.S.C. 154(b) by 89 days.

This patent is subject to a terminal disclaimer.

(21) Appl. No.: 16/248,703

(22) Filed: Jan. 15, 2019

(65) Prior Publication Data

US 2019/0167869 A1 Jun. 6, 2019

Related U.S. Application Data

(63) Continuation of application No. PCT/US2016/046913, filed on Aug. 12, 2016.

(51) Int. Cl.
*A61M 1/00* (2006.01)
*A61B 10/00* (2006.01)
(Continued)

(52) U.S. Cl.
CPC ....... *A61M 1/0094* (2014.02); *A61B 10/0045* (2013.01); *A61B 10/0096* (2013.01);
(Continued)

(58) Field of Classification Search
CPC .............. B01D 29/824; A61B 10/0096; A61B 10/0045; A61B 10/0283; A61M 1/0094;
(Continued)

(56) References Cited

U.S. PATENT DOCUMENTS

| 1,506,967 A | 9/1924 | Bosworth |
| 1,507,929 A | 9/1924 | Mosher |

(Continued)

FOREIGN PATENT DOCUMENTS

| JP | 2004-219278 | 8/2004 |
| SU | 1521464 A1 | 11/1989 |

(Continued)

OTHER PUBLICATIONS

Otomed® Bone Dust Collectors, as obtained by Archive.org on Jul. 23, 2016 and stored as http://www.gracemedical.com:80/sites/488/uploaded/files/LIT0177_CID_4682_OTOMED_Bone_Dust_Collectors_Sales_Sheet.pdf, 1 page, OTOMED®, Memphis, TN, USA.

(Continued)

*Primary Examiner* — Cameron J Allen
(74) *Attorney, Agent, or Firm* — Kevin E Flynn; Flynn IP Law

(57) ABSTRACT

A surgical collection assembly for filtering material from liquid obtained during surgery. A jar having an inlet and an outlet each adapted for connection to a suction line. A set of orientation features to position an upper portion of a collection basket within the jar such that an upper portion of the collection basket does not impede a flow of material entering the jar through the inlet. A bottom surface with a pattern of recessed paths in the bottom surface, the pattern of recessed paths connected to the outlet. A plunger assembly that may be reversibly attached to the jar so that a distal end of a plunger may be used to compress collected material within the collection basket to help remove fluid from the collected material. For certain uses, the surgical collection assembly may have a simple jar lid without an integrated plunger.

27 Claims, 25 Drawing Sheets

(51) Int. Cl.
  *B01D 29/82* (2006.01)
  *A61B 10/02* (2006.01)
(52) U.S. Cl.
  CPC ........ *A61M 1/0007* (2014.02); *A61M 1/0009* (2013.01); *A61M 1/0056* (2013.01); *B01D 29/824* (2013.01); *A61B 10/0283* (2013.01)
(58) Field of Classification Search
  CPC . A61M 1/0056; A61M 1/0009; A61M 1/0007
  See application file for complete search history.

(56) References Cited

U.S. PATENT DOCUMENTS

| | | | |
|---|---|---|---|
| 1,613,166 A | 1/1927 | Gregory | |
| 1,679,033 A | 7/1928 | Holmes | |
| 1,804,162 A | 5/1931 | Hehemann | |
| 1,919,031 A | 7/1933 | Muhleisen | |
| 2,053,021 A | 9/1936 | Cassol | |
| 2,125,532 A | 8/1938 | Wells | |
| 2,291,708 A | 8/1942 | Gluck | |
| 2,352,269 A | 6/1944 | Kraissl, Jr. | |
| 2,354,752 A | 8/1944 | Hellan | |
| 2,630,920 A | 3/1953 | Kerr | |
| 2,787,308 A | 4/1957 | Popeil | |
| 3,513,977 A | 5/1970 | Bellinson | |
| D255,480 S | 6/1980 | Zieg | |
| 4,240,570 A | 12/1980 | Brown et al. | |
| 4,261,359 A | 4/1981 | Chein | |
| 4,430,084 A | 2/1984 | Deaton | |
| 4,643,197 A | 2/1987 | Greene | |
| 4,744,955 A | 5/1988 | Shapiro | |
| 4,775,469 A | 10/1988 | Zimmerly | |
| 4,800,875 A | 1/1989 | Ray | |
| 4,922,902 A | 5/1990 | Wuchinich et al. | |
| 4,974,604 A | 12/1990 | Morris | |
| 5,049,273 A | 9/1991 | Knox | |
| 5,071,409 A | 12/1991 | Rosenberg | |
| 5,279,582 A | 1/1994 | Davison | |
| 5,407,565 A * | 4/1995 | Austin, Jr. ........... | A61C 17/065 210/188 |
| 5,478,586 A | 12/1995 | Connor | |
| 5,514,119 A | 5/1996 | Curtis | |
| 5,571,412 A | 11/1996 | Nerli | |
| 5,624,418 A | 4/1997 | Shepard | |
| 5,630,939 A | 5/1997 | Bulard et al. | |
| 5,753,112 A | 5/1998 | Barnes | |
| 5,766,134 A | 6/1998 | Lisak et al. | |
| 5,788,976 A | 8/1998 | Bradford | |
| 5,800,702 A | 9/1998 | Taylor-McCune et al. | |
| 5,887,510 A | 3/1999 | Porter | |
| 5,954,961 A | 9/1999 | Carchidi | |
| 6,007,496 A | 12/1999 | Brannon | |
| 6,022,354 A | 2/2000 | Mercuri et al. | |
| 6,299,763 B1 | 10/2001 | Ashman | |
| D450,106 S | 11/2001 | Herr | |
| 6,331,246 B1 | 12/2001 | Beckham et al. | |
| 6,347,756 B1 | 2/2002 | Dillard | |
| 6,387,070 B1 | 5/2002 | Marino | |
| 6,468,225 B1 | 10/2002 | Lundgren | |
| 6,494,869 B1 | 12/2002 | Hand et al. | |
| D502,531 S | 3/2005 | Liu | |
| 6,872,184 B2 * | 3/2005 | Brannon ............... | A61B 10/02 600/300 |
| 6,875,220 B2 | 4/2005 | Du et al. | |
| 7,040,218 B1 | 5/2006 | Biolchini, Jr. | |
| 7,163,618 B2 | 1/2007 | Beckham et al. | |
| 7,204,810 B2 | 4/2007 | Hynes et al. | |
| 7,214,059 B2 | 5/2007 | Takahashi | |
| 7,278,985 B2 | 10/2007 | Ågerup | |
| 7,497,340 B2 | 3/2009 | Hershberger et al. | |
| 7,531,092 B2 | 5/2009 | Hazlehurst | |
| 7,615,037 B2 | 11/2009 | Murray et al. | |
| 7,621,917 B2 | 11/2009 | Geneve et al. | |
| 7,758,556 B2 * | 7/2010 | Perez-Cruet ........ | A61F 2/4644 604/317 |
| 7,971,728 B2 | 7/2011 | Anspach et al. | |
| 8,088,291 B2 | 1/2012 | Hershberger et al. | |
| 8,092,427 B2 | 1/2012 | Urich et al. | |
| 8,485,986 B2 | 7/2013 | Lampropoulos et al. | |
| 8,518,002 B2 | 8/2013 | Murray et al. | |
| D690,813 S | 10/2013 | Bizzell | |
| D690,814 S | 10/2013 | Bizzell | |
| 8,622,953 B2 | 1/2014 | Hynes et al. | |
| 8,647,574 B2 | 2/2014 | Halverson et al. | |
| 8,740,908 B2 | 6/2014 | Farley et al. | |
| 8,790,321 B2 | 7/2014 | Segina et al. | |
| 8,815,099 B1 | 8/2014 | DuBois et al. | |
| 8,845,605 B2 | 9/2014 | Hensler et al. | |
| 8,915,897 B2 | 12/2014 | Murray et al. | |
| 8,920,393 B2 | 12/2014 | Hensler et al. | |
| 8,961,792 B2 | 2/2015 | Desai | |
| 9,034,044 B2 | 5/2015 | Hensler | |
| 9,555,169 B2 | 1/2017 | Segina et al. | |
| 9,636,235 B2 | 5/2017 | Hensler | |
| 9,693,843 B2 | 7/2017 | Cohen | |
| 9,731,064 B2 | 8/2017 | Ruiz Soto et al. | |
| 9,872,944 B1 | 1/2018 | Willard et al. | |
| 10,232,084 B1 | 3/2019 | Boozari | |
| 2002/0132369 A1 | 9/2002 | Wilkinson et al. | |
| 2004/0167529 A1 | 8/2004 | Papendick et al. | |
| 2005/0055077 A1 | 3/2005 | Marco et al. | |
| 2006/0052760 A1 | 3/2006 | Batzdorf | |
| 2006/0086656 A1 | 4/2006 | Morgan | |
| 2006/0173426 A1 | 8/2006 | Urich et al. | |
| 2006/0270974 A1 | 11/2006 | Goff et al. | |
| 2007/0016100 A1 | 1/2007 | Miller | |
| 2007/0028779 A1 | 2/2007 | Pigliacampo et al. | |
| 2007/0203471 A1 | 8/2007 | Anspach et al. | |
| 2007/0225665 A1 | 9/2007 | Perez-Cruet | |
| 2008/0071192 A1 | 3/2008 | Hynes et al. | |
| 2008/0097390 A1 | 4/2008 | Dacquay et al. | |
| 2008/0217264 A1 | 9/2008 | Leach et al. | |
| 2008/0290050 A1 | 11/2008 | Reis, Jr. | |
| 2009/0306669 A1 | 12/2009 | Takahashi | |
| 2010/0005979 A1 | 1/2010 | Baccetti | |
| 2010/0255484 A1 | 10/2010 | Halverson et al. | |
| 2010/0275785 A1 | 11/2010 | Weissman et al. | |
| 2011/0056385 A1 | 3/2011 | McLean et al. | |
| 2011/0064611 A1 | 3/2011 | Cioanta et al. | |
| 2011/0301496 A1 | 12/2011 | Lampropoulos et al. | |
| 2012/0129933 A1 | 5/2012 | Wolf | |
| 2012/0220925 A1 | 8/2012 | Seegert et al. | |
| 2014/0249513 A1 | 9/2014 | Howard et al. | |
| 2014/0288534 A1 | 9/2014 | Howard et al. | |

FOREIGN PATENT DOCUMENTS

| | | |
|---|---|---|
| WO | 1994/17752 A1 | 8/1994 |
| WO | 2003073945 A1 | 9/2003 |
| WO | 2005/079947 A2 | 9/2005 |
| WO | 2006/023156 A2 | 3/2006 |
| WO | 2009/06498 A1 | 5/2009 |
| WO | 2012154514 A1 | 11/2012 |

OTHER PUBLICATIONS

ThompsonMIS BoneBac Press, as obtained by Archive.org on Mar. 6, 2016 and stored at http://web.archive.org/web/20160306193139/http://thompsonmis.com/products/bonebac-press/, 3 pages as printed (third page blank), NOTE-stored web page has a series of six images that alternate and links to three videos so please access the live page rather than the static printout, Thompson MIS, Londonderry, NH, USA.

Ki Yun Cho, PCT Written Opinion of the International Searching Authority for parent application PCT/US2016046913, dated May 11, 2017, 7 pages, Korean Intellectual Property Office, Daejeon, South Korea.

Ki Yun Cho, PCT International Search Report for parent application PCT/US2016046913, dated May 11, 2017, 4 pages, Korean Intellectual Property Office, Daejeon, South Korea.

(56) References Cited

OTHER PUBLICATIONS

Grieb, Christian, Supplementary European Search Report for EP 16 91 2861 (which shares a common priority with the present application), dated Feb. 20, 2020, 8 pages, European Patent Office, Munich, Germany.
Kobayashi, Mutsumu, Japanese Office Action for Application No. 2019-529138 (which shares a common priority with the present application), dated Jul. 28, 2020, 5 pages, Japanese Patent Office.
Racine, Russel M., Defendant's Preliminary Invalidity Contentions regarding U.S. Pat. No. 10,493,183 filed in the Unite States District Court for the Eastern District of North Carolina—Southern Division Case 7:19-CV-240-FL, May 15, 2020, 155 pages, Cranfill Sumner & Hartzog LLP, Charlotte, North Carolina.

* cited by examiner

100

100

420

420

420

420

9       9

420

FIG. 18
420
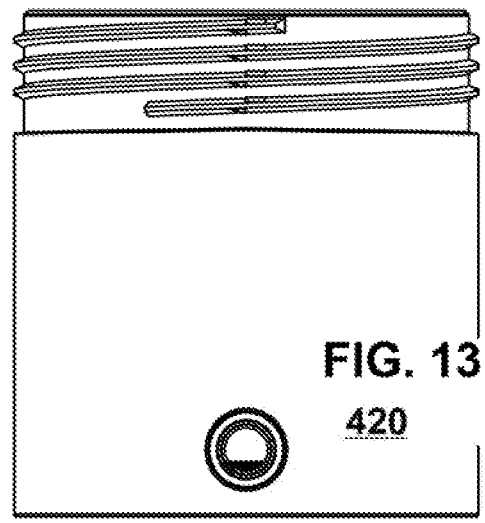
FIG. 13
420
FIG. 19
420
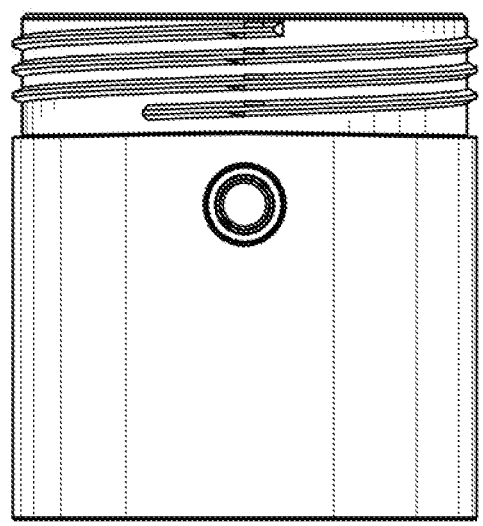

420

420

454

454

164

454

454

454

454

454

480

480

480

480

480

480

480

480

COLLECTION JAR AND COLLECTION BASKET FOR SURGICAL USE

This application claims priority to commonly owned Patent Cooperation Treaty Patent Application No. PCT/US2016/046913 filed Aug. 12, 2016 for Collection System for Surgical Use, the '913 application is incorporated by reference herein. A related application that also claims priority to the '913 application is U.S. patent application Ser. No. 15/682,344, now issued as U.S. Pat. No. 9,872,944 for Collection System for Surgical Use.

BACKGROUND

Field of the Disclosure

This disclosure relates generally to systems that collect surgical samples via suction and filtration.

Terminology

Or—Unless explicit to the contrary, the word "or" should be interpreted as an inclusive or rather than an exclusive or. Thus, the default meaning of or should be the same as the more awkward and/or.

Specimen Collection—The term should be read broadly to include anything that might be collected and analyzed in pathology through biopsy or other processes.

Tissue—The term tissue should be read expansively to include any portion of a patient that may be removed from the surgical site by suction and then separated from fluids by filtration. This may include pieces of bone, organs, muscle, or other matter. The material gathered may include foreign substances that were introduced into the patient.

Patient—The term patient should be read expansively to include humans, cadavers undergoing autopsies or used in training, and animals undergoing a surgical procedure.

SUMMARY OF THE DISCLOSURE

Aspects of the teachings of the present disclosure may be stated as a surgical collection assembly for filtering material from liquid obtained during surgery; the surgical collection assembly having a jar. The jar having:
an open end that may be reversibly sealed with a jar top;
an inlet adapted for connection to a suction line;
an outlet adapted for connection to a suction line;
a set of orientation features to position an upper portion of a collection basket within the jar such that an upper portion of the collection basket does not impede a flow of material entering the jar through the inlet;
a bottom surface with a pattern of recessed paths in the bottom surface, the pattern of recessed paths connected to the outlet;

The surgical collection assembly also having a collection basket with sidewalls and a bottom connected to an upper portion of the collection basket so that the upper portion of the collection basket can be used to position the collection basket within the jar.

The surgical collection assembly also having a plunger assembly. The plunger assembly having a jar top that can be reversibly connected to the open end of the jar; the jar top having a bore that allows a plunger rod with a distal end to move relative to the jar top so that a distal end of a plunger may be used to compress collected material within the collection basket to help remove fluid from the collected material.

The plunger assembly also having a plunger with a distal end to compress collected material and a plunger rod to pass through the bore in the jar top so a proximal end of the plunger may be moved by a user.

The surgical collection assembly adapted to allow suction applied to the outlet of the jar to pull liquid and non-liquid material through a tube connected to the inlet of the jar; the liquid and non-liquid material passing into the collection basket with much of the liquid leaving the collection basket through at least a portion of the collection basket to enter the pattern of recessed paths in the bottom surface and then out the outlet leaving a filtered portion of the non-liquid material in the collection basket.

For certain uses, the surgical collection assembly may have a simple jar lid without an integrated plunger.

Aspects of the teachings of the present disclosure may be summarized as a method for gathering collected material from a surgical procedure and compressing the collected material to remove fluid. The method including inserting a first collection basket into a collection jar. The collection jar having an inlet and an outlet. The collection jar outlet in fluid communication with a recessed pattern in a basket side of a bottom of the collection jar. Applying suction to the outlet will pull material through inlet tubing connected to the inlet, the material passing through the inlet, with at least some fluid in the material passing through the first collection basket and into the recessed pattern then to the outlet to leave filtered material in the first collection basket. The step of inserting the first collection basket into the collection jar guided by an interaction of the collection jar and the first collection basket precluding placement of a set of at least one basket handle in a position that obstructs the inlet.

The method including placing a plunger assembly onto the collection jar; connecting inlet tubing to the inlet; and connecting outlet tubing to the outlet. The order of these three actions not material to the method.

The method including applying suction to the outlet tubing connected to the outlet so that whenever a non-jar end of the inlet tubing is placed into a surgical site, fluids and small materials are pulled through the inlet tubing through the inlet and into the first collection basket.

The method including removing a non-jar end of the inlet tubing from the surgical site and using the plunger assembly to move a distal end of a plunger downward to compress materials collected in the first collection basket.

Removing the plunger assembly from the collection jar while the inlet tubing is still connected to the inlet and the outlet tubing is still connected to the outlet and removing the first collection basket with compressed material from the collection jar.

Repeating the process with a second collection basket which may be the first collection basket after material is removed from the first collection basket.

Additional aspects of the teachings contained within this disclosure are addressed in the claims submitted with this application upon filing. Rather than adding redundant restatements of the contents of the claims, these claims should be considered incorporated by reference into this summary.

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provide below as one of skill in the art will recognize that inventive concepts illustrated in various examples can be combined together in order to address a specific application.

Other systems, methods, features and advantages of the disclosed teachings will be immediately apparent or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The disclosure can be better understood with reference to the following figures. The components in the figures are not necessarily to scale, emphasis instead being placed upon illustrating the principles of the disclosure. Moreover, in the figures, like reference numerals designate corresponding parts throughout the different views.

FIG. 18 is a left side view of jar 420.

FIG. 19 is a right side view of jar 420.

DETAILED DESCRIPTION

Figure 1:
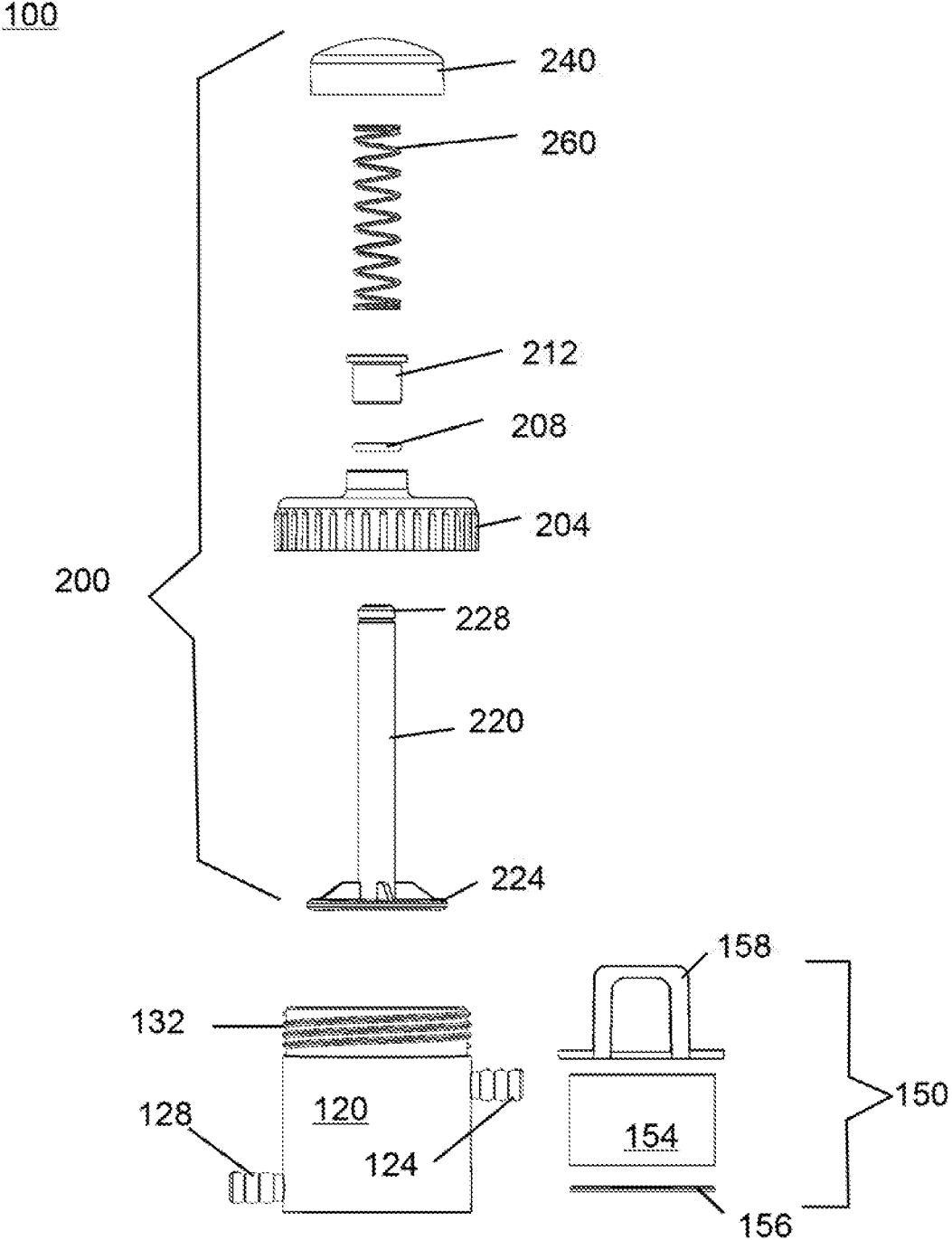
FIG. 1 shows an exploded front view of a surgical collection assembly 100.

FIG. 1 shows an exploded front view of a surgical collection assembly 100. Visible in FIG. 1 are jar 120 with inlet 124 and outlet 128. The inlet 124 and outlet 128 may have a shape designed to retain tubing such as a barbed profile. Jar 120 has a set of male threads 132 for engaging a corresponding set of female threads 216 (not shown here) within cap 204.

A basket ring 158 is used to position a basket 150 within the jar 120 to allow the basket to collect material filtered from a flow of suctioned material taken from the surgical site. The basket 150 may be constructed so that a basket sidewall 154 is connected to a basket bottom 156. The cylindrical shape of the basket 150 may be maintained by a bottom ring 164 which maintains the flat basket bottom 156 relative to the substantially cylindrical basket sidewall 154. The flat basket bottom 156 is sized to fit within an area defined by the inside perimeter of the bottom ring 164. Thus the basket 150 is substantially cylindrical and maintains predictable gaps between the outer surface of the basket bottom 156 and the bottom surface 190 of the jar 120 and between the outer surface of the basket sidewall 154 and ribs 136 and 140 of the jar 130.

Suction applied to the outlet 128 of the jar 120 through suction side tubing (not shown) pulls material from the surgical site into surgical side tubing (not shown) into the inlet 124 of jar 120 and into the basket 150. Suction pressure removes much of the liquid content of the material provided to the basket 150 as the basket 150 serves as a filter to separate non-liquids from the liquid removed from the surgical site.

A plunger assembly 200 has plunger rod 220 with a broad distal end 224 that may be moved to compress the contents of the basket 150 to remove additional fluids from the collected material. The plunger rod 220 has a proximal end 228 that fits through a bore 232 (not visible here). The bushing 212 and O-ring 208 help maintain a vacuum seal around the plunger rod 220. The bushing 212 is press fit into the bore 232 to capture the O-ring 208 to tightly fit around plunger rod 220 and inside the bore to provide an adequate vacuum seal. The vacuum seal does not need to be perfect, but should be sufficient so that suction applied to the outlet 128 to provide suction to the inlet 124 is sufficient for use in pulling material from the surgical site. If the opening at the surgical site is covered by something that cannot be pulled into the opening, then the suction may pull some air through the seal around the plunger rod 220 but small quantities of in-leakage is not a problem.

The proximal end 228 of plunger rod 220 fits through the interior of spring 260 and into a bore in plunger rod handle 240. The connection between the proximal end 228 of the plunger rod 220 and the bore in the plunger rod handle 240 may be made in a number of ways. The connection may be a threaded connection and thus reversible. The connection may be a non-reversible connection made via any of number of techniques known to those of skill in the art including a snap fit. Gluing may be used instead of a snap-fit if there is a desire for a secure connection.

The spring 260 holds the plunger rod 220 in an elevated position with the distal end 224 of the plunger rod 220 above the flow of material entering the jar 120 through the inlet 124. The plunger rod handle 240 may be pushed down against the spring force to push the distal end 224 of the plunger rod 220 downward to compress material collected in the basket 150 to further remove fluid.

Figure 2:
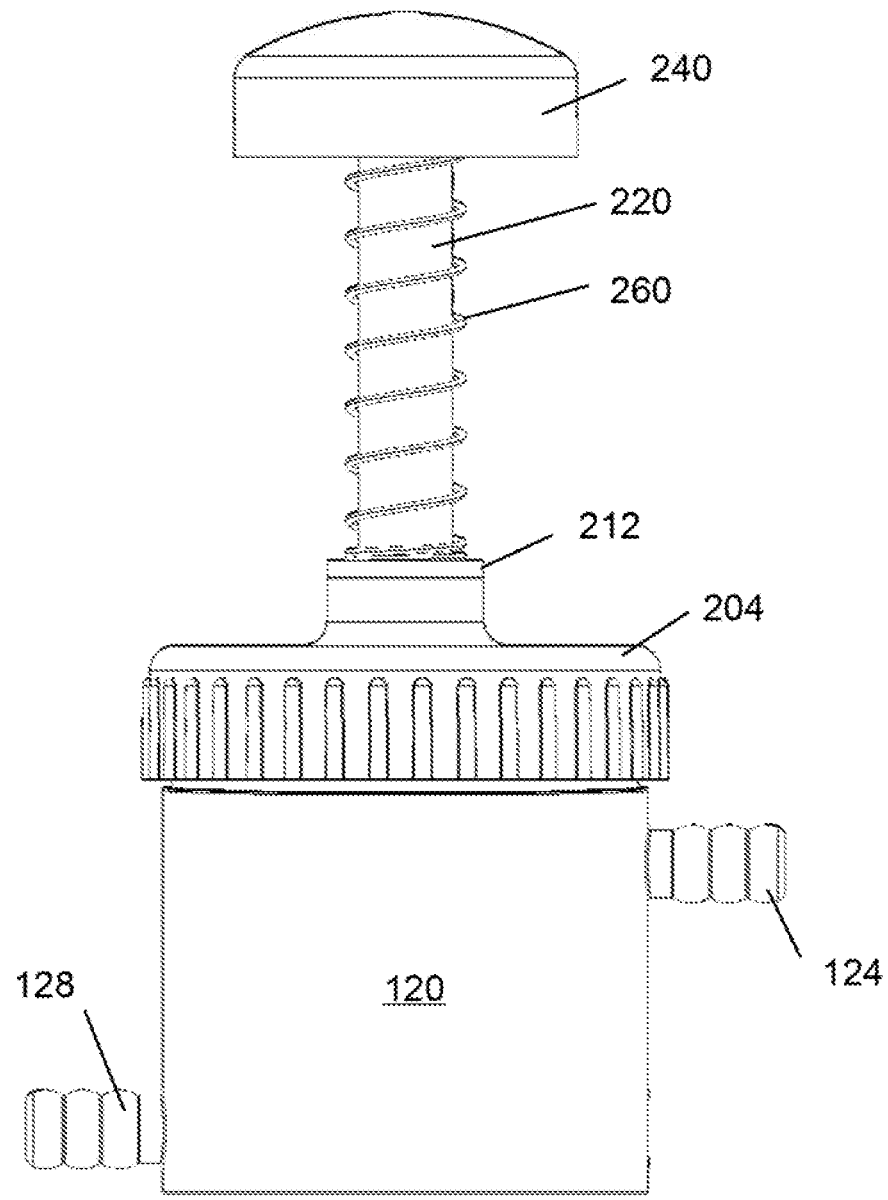
FIG. 2 provides a front view of the surgical collection assembly 100.
Figure 3:
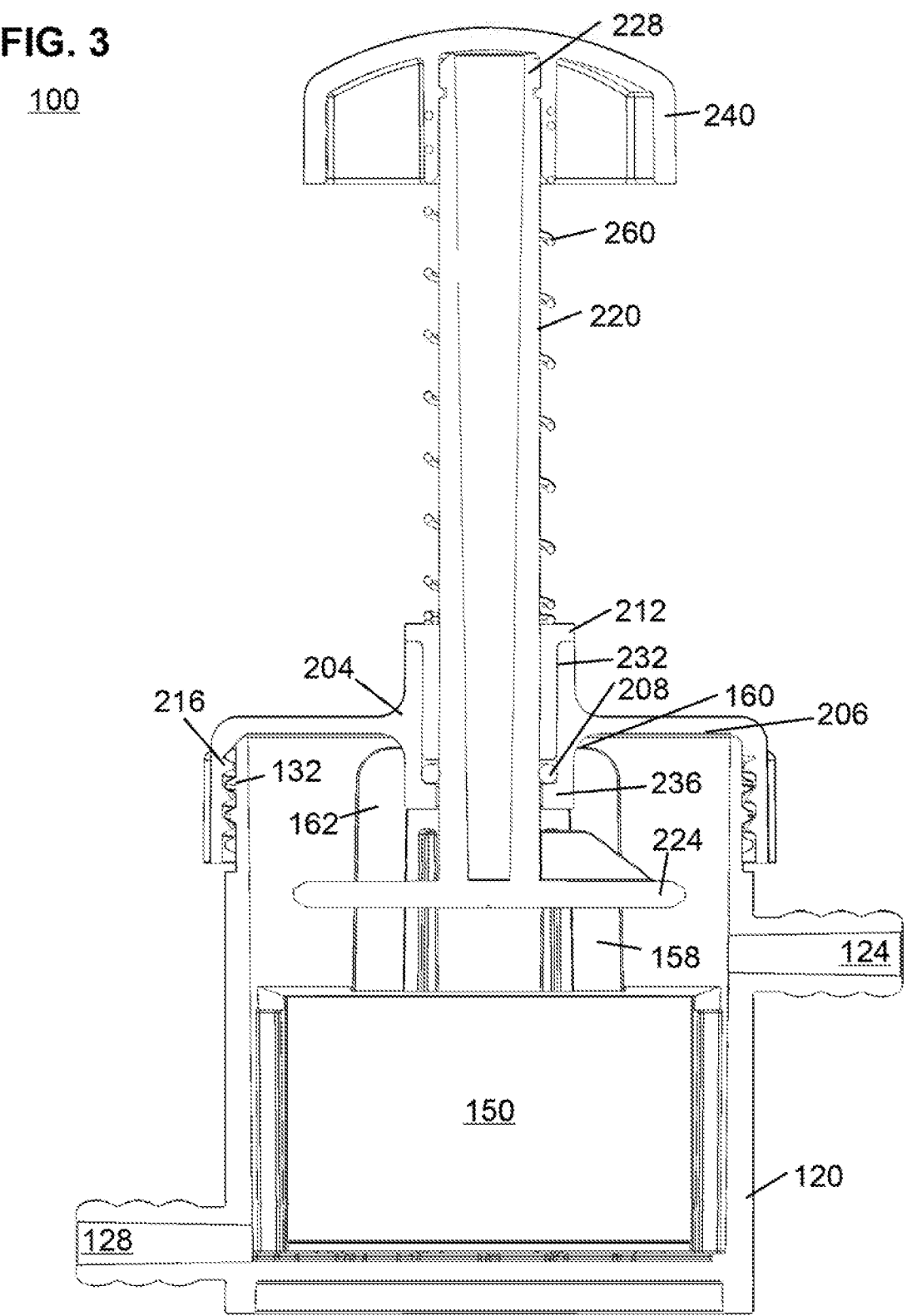
FIG. 3 shows a cross section of the view from FIG. 2 taken through the midlines of the inlet 124 and outlet 128.

FIG. 2 provides a front view of the surgical collection assembly 100. FIG. 3 shows a cross section of the view from FIG. 2 taken through the midlines of the inlet 124 and outlet 128.

Visible in FIG. 2 and FIG. 3 are previously referenced elements: plunger rod handle 240, plunger rod 220, spring 260, bushing 212, cap 204, inlet 124, jar 120, and outlet 128.

Additional elements visible in FIG. 3 that are not visible in FIG. 2 include: O-ring 208 resting on ledge 236 in bore 232, proximal end 228 of plunger rod 220, distal end 224 of plunger rod 220, basket ring 158, basket 150, female threads 216 on cap 204, and male threads 132 on jar 120.

Note that FIG. 3 provides a view of the seal around the plunger rod 220 as the bushing 212 encloses the O-ring 208 between the bushing 212 and the ledge 236 within the bore 232 of the cap 204.

A careful observer will note that the model shows the O-ring 208 in the shape it assumes before engagement with the uncapped plunger rod 220. The O-ring is compressed between the plunger rod 220 and the cap 204. However, the bushing 212 is not designed to compress the O-ring 208.

Figure 4:
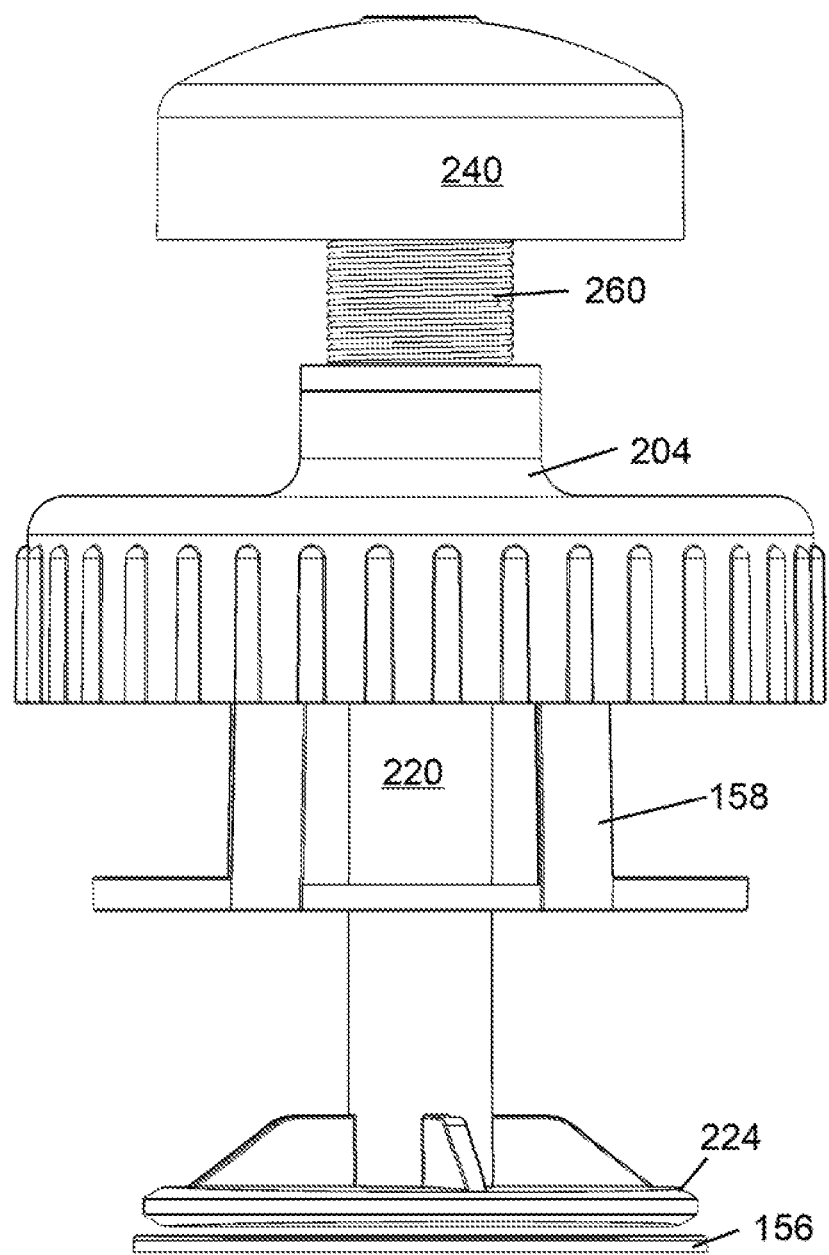
FIG. 4 shows the plunger rod 220 moved downward so that the distal end 224 of the plunger rod 220 is just above the basket bottom 156.

FIG. 4 shows the plunger rod 220 moved downward so that the distal end 224 of the plunger rod 220 is just above the basket bottom 156. Force applied to the plunger rod handle 240 has compressed the spring 260. Also visible in this view is cap 204 and basket ring 158. In order to show the relationship between the distal end 224 of the plunger rod 220 and the basket bottom 156, the jar 120 and sidewalls of the basket 150 have been made invisible.

After releasing the plunger rod handle 240, the distal end 224 of the plunger rod 220 will move upward relative to the basket 150 as the spring force is sufficient to return the plunger rod handle 240 to the upper position. It is possible that during the compression of collected material that some collected material may fill any void between the outer perimeter of the distal end 224 of the plunger rod 220 in the inner perimeter of the basket 150. To minimize any tendency to lift the basket 150 out of position, the basket ring 158 has a pair of handles 162 (one handle visible in FIG. 3). The top edge 160 of the handle 162 is positioned very close to the inside face 206 of the cap 204 so that the distal end 224 of the plunger rod 220 continues to move upward after the top edge 160 of the handle 162 strikes the inside face 206 of the cap 204 so that the basket 150 becomes dislodged from the distal end 224 of the plunger rod 220.

Placement of Inlet and Outlet on Jar.

Note that by having both the inlet 124 and the outlet 128 located on the jar 120 and not split between the jar 120 and the cap 204, the rotating the plunger & cap assembly 200 to remove the plunger & cap assembly 200 to expose the interior of the jar 120 may be done without disconnecting the vacuum side tubing connecting the outlet 128 to the vacuum source and without disconnecting the surgical side tubing connected to the inlet 124. Thus neither the connection of tubing to the inlet 124 or to the outlet 128 needs to be a more expensive quick disconnect connection such as a bayonet connection.

Allowing quick removal of the plunger & cap assembly 200 from the surgical collection assembly 100 to expose the basket 150 allows collected material to be removed and a new basket 150 to be inserted. As the connections to the inlet 124 and outlet 128 are in place, the process of collecting can resume quickly after the plunger & cap assembly 200 is re-engaged with the jar 120.

A second advantage of having the inlet 124 on the jar 120 rather than on the cap 204 is that this placement helps keep material coming in through the inlet from getting up on the top side of the broad distal end 224 of the plunger rod 220. This avoids wasting material that could have been collected in the basket 150 and reduces the opportunity for material to interfere with the operation of the plunger rod 220.

When using the plunger rod 220 to press the collected material, an operator may wish to lift the surgical end of the surgical side tubing out of the surgical site so that only air is entering the inlet 124. The suction source may be left on during this process to help remove fluids that are pressed out of the collected material.

Figure 5:
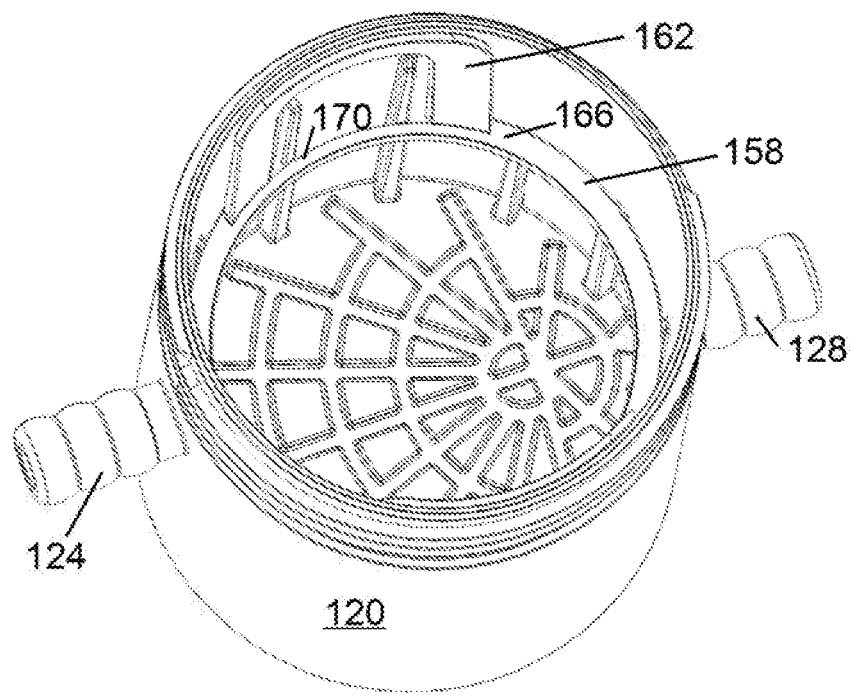
FIG. 5 is top front perspective view of the jar 120.
Figure 6:
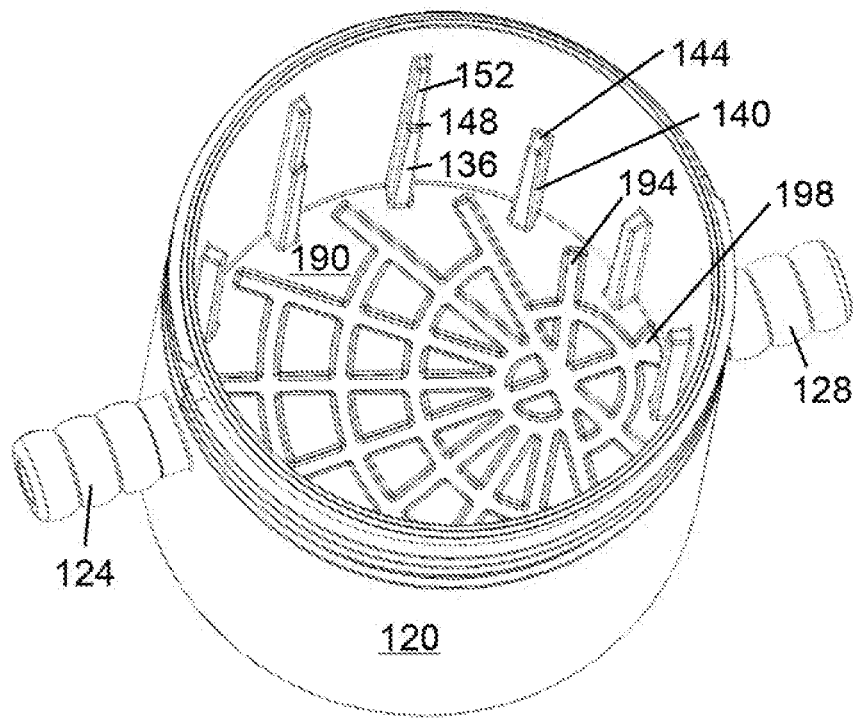
FIG. 6 is the same view as FIG. 5 but the basket ring 158 is removed so that the portions of the jar 120 that support and position the basket ring 158 may be seen.

FIG. 5 is top front perspective view of the jar 120. For purposes of illustration, a basket ring 158 is visible in FIG. 5, but the basket ring 158 does not have a basket sidewall 154 or basket bottom 156. FIG. 6 is the same view as FIG. 5 but the basket ring 158 is removed so that the portions of the jar 120 that support and position the basket ring 158 may be seen.

The basket ring 158 may be described as a pair of handles 162. Between the handles 162 are portions of the basket ring 158 that may be called inter-handle segments 166. The inter-handle segments 166 may be distinguished from the intra-handle segments 170 which may be thinner than the inter-handle segments 166.

The difference between the intra-handle segments 170 and the inter-handle segments 166 allows the basket ring 158 to be oriented within the jar 120 to avoid blocking the inlet 124. The jar 120 orients the basket ring 158 by locating long ribs 136 and short ribs 140. The inter-handle segments 166 may rest on short rib ledges 144 but are too wide to be aligned with the long ribs 136. In contrast, the narrower intra-handle segments 170 can fit inside the perimeter formed by the upper portions 152 of the long ribs 136 and rest upon the long rib ledges 148.

Recessed Pattern.

As noted in FIG. 6 the jar 120 has a bottom surface 190 that supports the bottom surface of the basket 150 including when the plunger rod 220 is compressing material within the basket 150. A recessed pattern 194 fans out from the outlet mouth 198 so that suction pulling on the outlet 128 applies suction pressure throughout the recessed pattern 194 to pull liquids from the basket 150 and draw the liquid to the outlet mouth 198 and out the outlet 128. The pattern used for the recessed pattern 194 does not need to be identical to the pattern shown here. A number of different patterns are possible. While symmetry on either side of a midline between the inlet 124 and 128 may be a natural choice, this is not required. The width and depth of the recessed pattern does not need to be uniform. A pattern that allows suction to reach a distal end of the pattern even if a small obstruction is lodged in a portion of the pattern has advantages over a pattern that lacks the cross links that allow for alternate routes for drainage.

Figure 7:
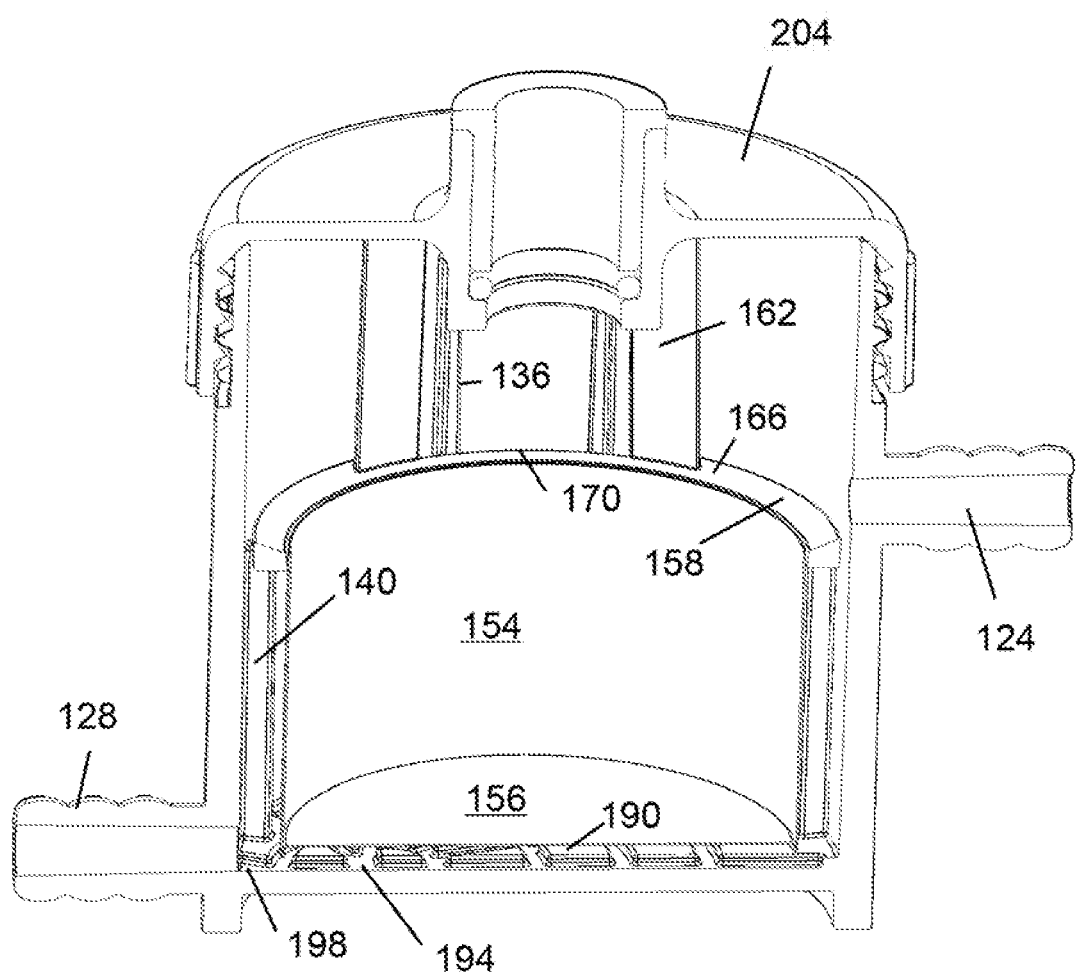
FIG. 7 shows a cross section of the jar 120 taken again through the inlet 124 and outlet 128.

FIG. 7 shows a cross section of the jar 120 taken again through the inlet 124 and outlet 128. The cross section has been rotated to move the cap 204 towards the observer to allow bottom surface 190, recessed pattern 194, and outlet mouth 198 to be visible relative to the basket 150 and in particular to the basket bottom 156. Notice that the combination of the basket ring 158, long ribs 136 and short ribs 140 impede flow from the inlet 124 to the outlet 128 that passes around the perimeter of the basket 150. Having the distal ends of the recessed pattern 194 terminate beyond the outer edges of the basket 150 provides suction beneath the basket ring 158 to pull fluids from the basket sidewalls 154 in addition to pulling fluid from the basket bottom 156.

Basket Formation.

A variety of techniques may be used to make a basket and basket ring assembly in keeping with the teachings of this disclosure. As noted above, the basket may be made of a sidewall joined to a bottom. The connection of the sidewall to the bottom may be connected via stitching. Alternatively, the connection of the sidewall to the bottom may be accomplished by placing a flexible ring at the bottom perimeter of the basket and connecting both the sidewall and the bottom to the flexible ring. The connection may be via stitching, over molding, heat sealing, or some other connection process that is suitable for use in collecting bone material that will be used in a surgical procedure. The connection to the basket ring may be heat staked, welded, or connected via adhesive. The bottom may be on the same plane as the bottom edge of the sidewalls.

Having a basket 150 which is flexible allows the basket bottom 156 and bottom ring 164 to be moved relative to the basket ring 158 so that the basket 150 is inverted to that that interior surfaces of the basket 150 during collection become the outer surfaces of the basket 150 during delivery of collected material.

The basket material will be chosen by the designer as part of the total design but a basket made of material that has open area in the range of 47% with a mesh opening in the range of 200 micrometers may be used with certain baskets and applications. For context, 200 micrometers (also known as microns) is the type of filtration that might be used to remove fine sand from a liquid.

Those of skill in the art will appreciate that the disclosed surgical collection assembly 100 provides a basket with extensive filter surface area that allows for continuous filtration throughout the collection process. The large surface area of the basket and other features of the disclosed surgical collection assembly 100 make the assembly resilient to the presence of material that might clog and impair another collection system.

The mobility of the basket is also important to allow collected material to be moved to prep table, while allowing a cap to be placed back on and regular suction to be continued.

Alternatives and Variations.

Alignment of Inlet and Outlet.

The jar 120 has been shown with the inlet 124 to the outlet 128 offset by 180 degrees. This offset is believed to be useful because it allows for captured product to fill the entire basket because flow is across the diameter of the basket. If ports were on the same side, you may have product build up on one side of the basket. By having the inlet 124 arranged above the basket and the outlet pulling material from below the basket, the surgical collection assembly 100 is not reliant on gravity as the suction force is sufficient to promote proper operation even in the event that the jar 120 is knocked over so it is horizontal rather than vertical.

While there are advantages to having the inlet 124 to the outlet 128 offset by 180 degrees, there would be similar advantages with something less than a 180 degree offset. Even 90 degrees would provide substantial advantages. Those of skill in the art will appreciate that a surgical collection assembly 100 with an inlet 124 located directly above the outlet 128 would be a viable collection device even if such a collection device did not have the suggested 180 degree offset.

Having the outlet 128 located near the bottom of the jar 120 increases the ability of the collection device to be cleared of fluid relative to the use of the same suction source with an outlet placed close to the top of the jar.

Specimen Collection Lid.

The jar 120, basket 150 with basket ring 158 may be used with an alternative cap 304 that does not have a bore for use with a plunger rod but is a solid top. This alternative cap 304 may be used when the jar 120 and basket 150 are employed to filter out material taken via suction from a surgical site. This material may be bone which is prepared and reused but is more likely to be material to be collected and sent for analysis.

Figure 8:
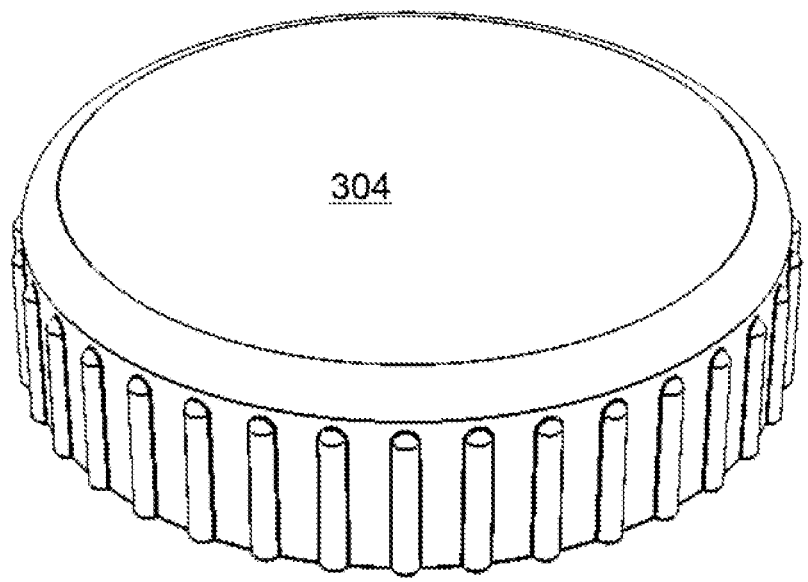
FIG. 8 provides a top perspective view of alternative cap 304, including female threads 216 to engage corresponding male threads 132 of the jar 120.
Figure 9:
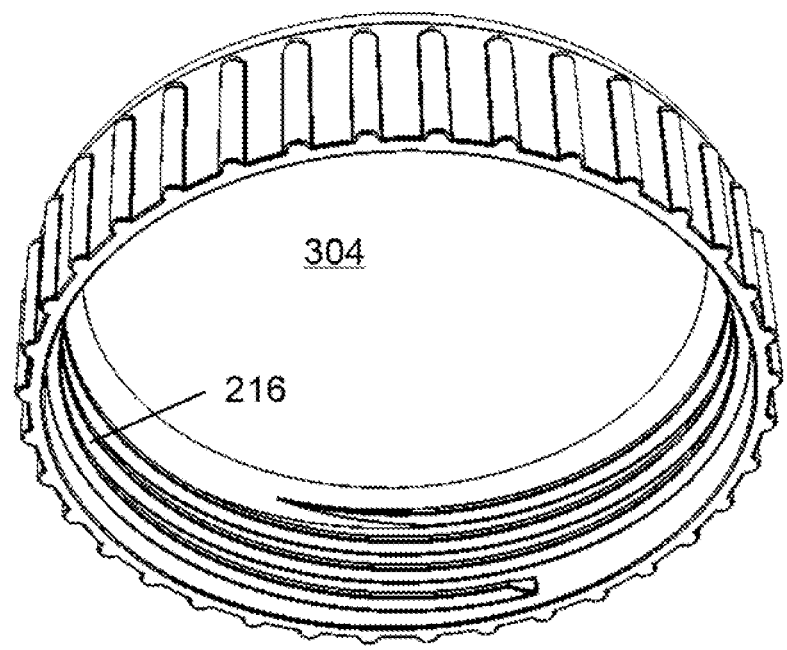
FIG. 9 provides a bottom perspective view of alternative cap 304, including female threads 216 to engage corresponding male threads 132 of the jar 120.

FIG. 8 and FIG. 9 provide a top and bottom perspective view of alternative cap 304, including female threads 216 to engage corresponding male threads 132 of the jar 120.

Alternative Way to Avoid Blocking the Inlet.

Disclosed above was a method to orient the basket ring to avoid interfering with the ingress of suction material passing from the inlet into the interior of the basket. The basket ring was oriented using an interaction between the basket ring 158 and the short rib ledges 144 and long rib ledges 148.

Figure 10:
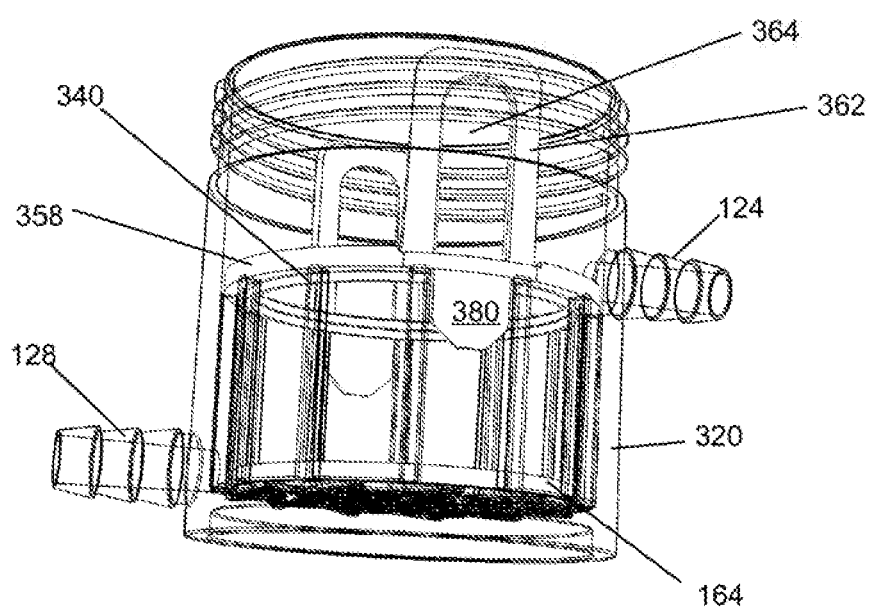
FIG. 10 provides a view of jar 320 as set to transparent to allow view of the basket ring 358.
Figure 25:
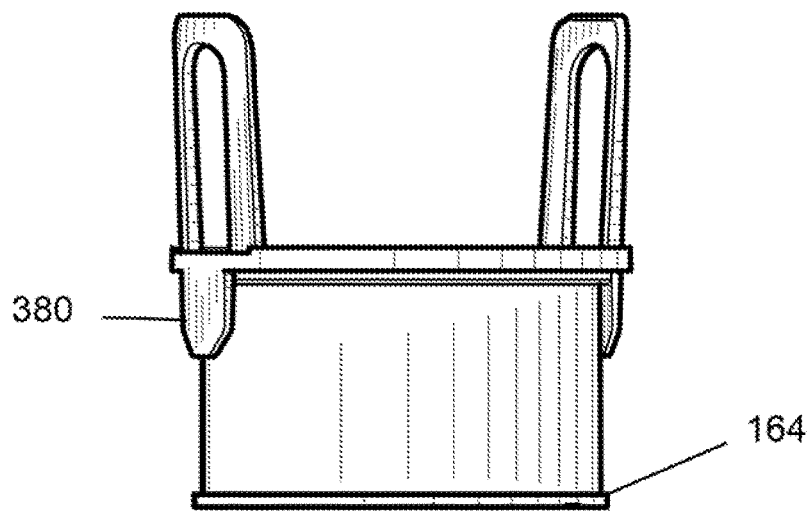
FIG. 25 is a front, left perspective view of basket 454.
Figure 26:
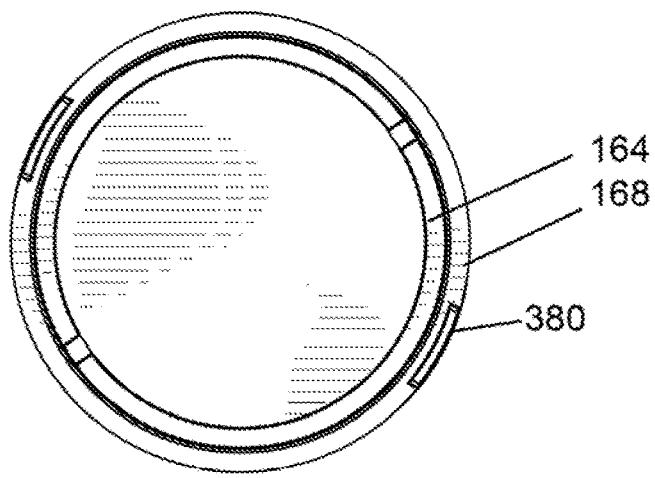
FIG. 26 is a bottom plan view of basket 454.

An alternative way to orient a basket ring 358 within jar 320 is disclosed. FIG. 10 provides a view of jar 320 as set to transparent to allow view of the basket ring 358. Basket 150 is shown with just the basket bottom 156 visible to avoid obstructing views of the ribs 340. The basket ring 358 rests on a set of rib ledges 344. The rib ledges 344 on the top of the set of ribs 340 set the height of the basket ring 358. A set of one or more orientation tab 380 sets the orientation of the basket ring 358 so that the one or more handles 362 are in defined positions with respect to the set of ribs 340. As shown in FIG. 10 there are a pair of handles 362 and they can be place in a number of positions including having one handle 362 placed between the ribs 340 on either side of the inlet 124. The handle opening 364 is sized so that the flow of material coming into the jar 320 from the inlet 124 would pass through the handle opening 364 and the handle 362 would not serve as an impediment. As best seen in FIG. 25 and FIG. 26, the orientation tabs 380 do not interfere with the movement of the basket bottom 156 up to the bottom side of the basket ring 158 when the basket is inverted to empty out collected contents.

One of skill in the art will appreciate that additional short ribs may be placed on the sidewall of the jar 320 to prevent a choice of putting the handle 362 near the inlet so that the handle opening 364 would not need to be sized to accommodate flow through the handle opening 364.

While placing the orientation tabs 380 beneath the handles 362 is one approach, the orientation tabs 380 could be placed elsewhere. There does not need to be a one to one correspondence between the number of orientation tabs and the number of handles.

Figure 11:
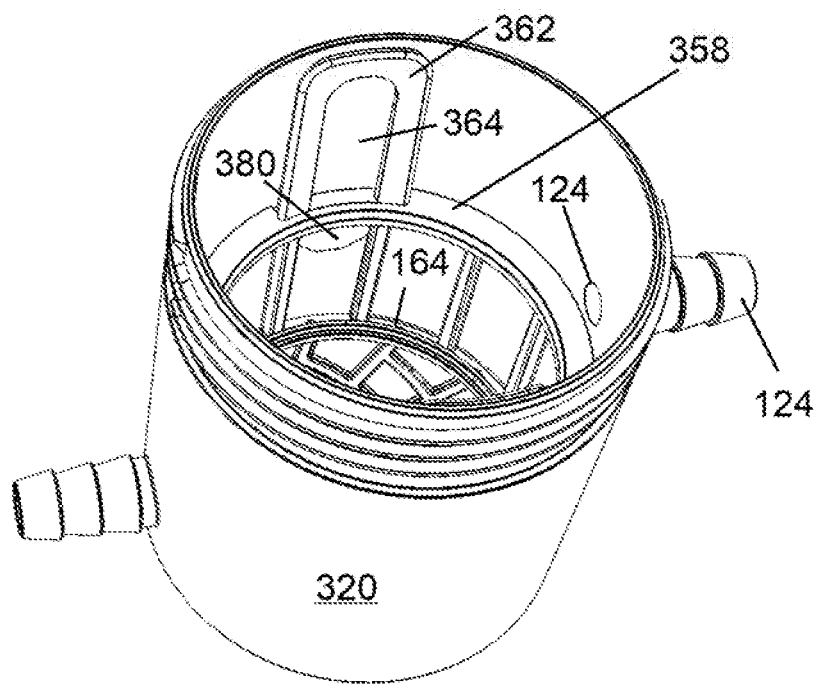
FIG. 11 is a top perspective view of jar 320 showing basket ring 358 but not the basket.
Figure 12:
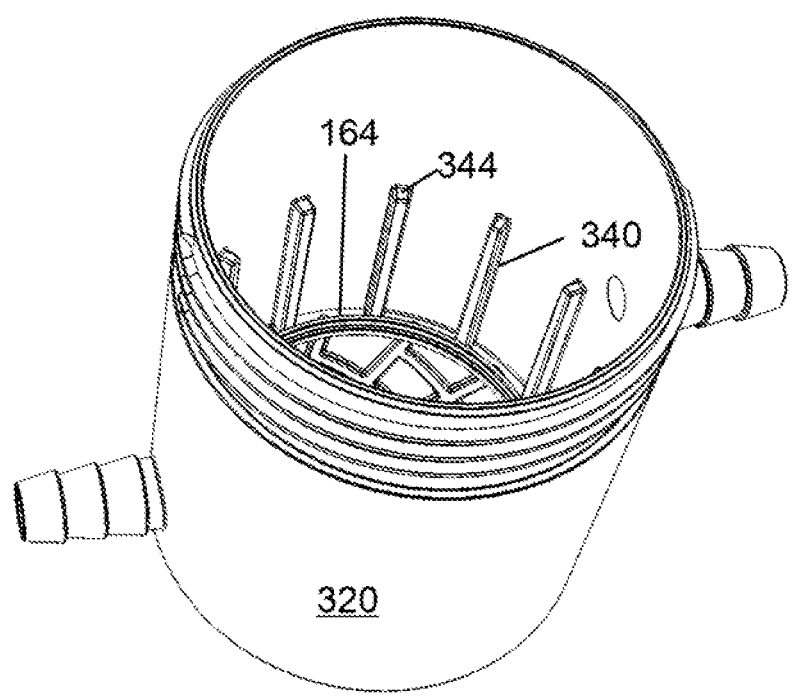
FIG. 12 is a top perspective view of jar 320 without the basket ring 358 shown in FIG. 11.

FIG. 11 and FIG. 12 show the jar 320 as a solid object. The basket is rendered invisible to allow the ribs 340 and rib ledges 344 to be visible. The difference between FIG. 11 and FIG. 12 is the basket ring 358 is made invisible in FIG. 12.

Jar 320 and basket 150 may be used with plunger & cap assembly 200 if the material collected in the basket 150 is to be compressed while in the jar 320 or may be used with an alternative cap 304 if there is no intent to use a plunger to compress the collected material in the jar 320.

The basket and rib concept introduced through FIG. 10, FIG. 11, and FIG. 12 may be used with jar 420 and basket 454. A set of drawings shows these components without the clutter of lead lines and element numbers. A set of drawings without lead lines and element numbers shows a plunger & cap assembly 480 that may be used with jar 420 and basket 454.

Figure 13:
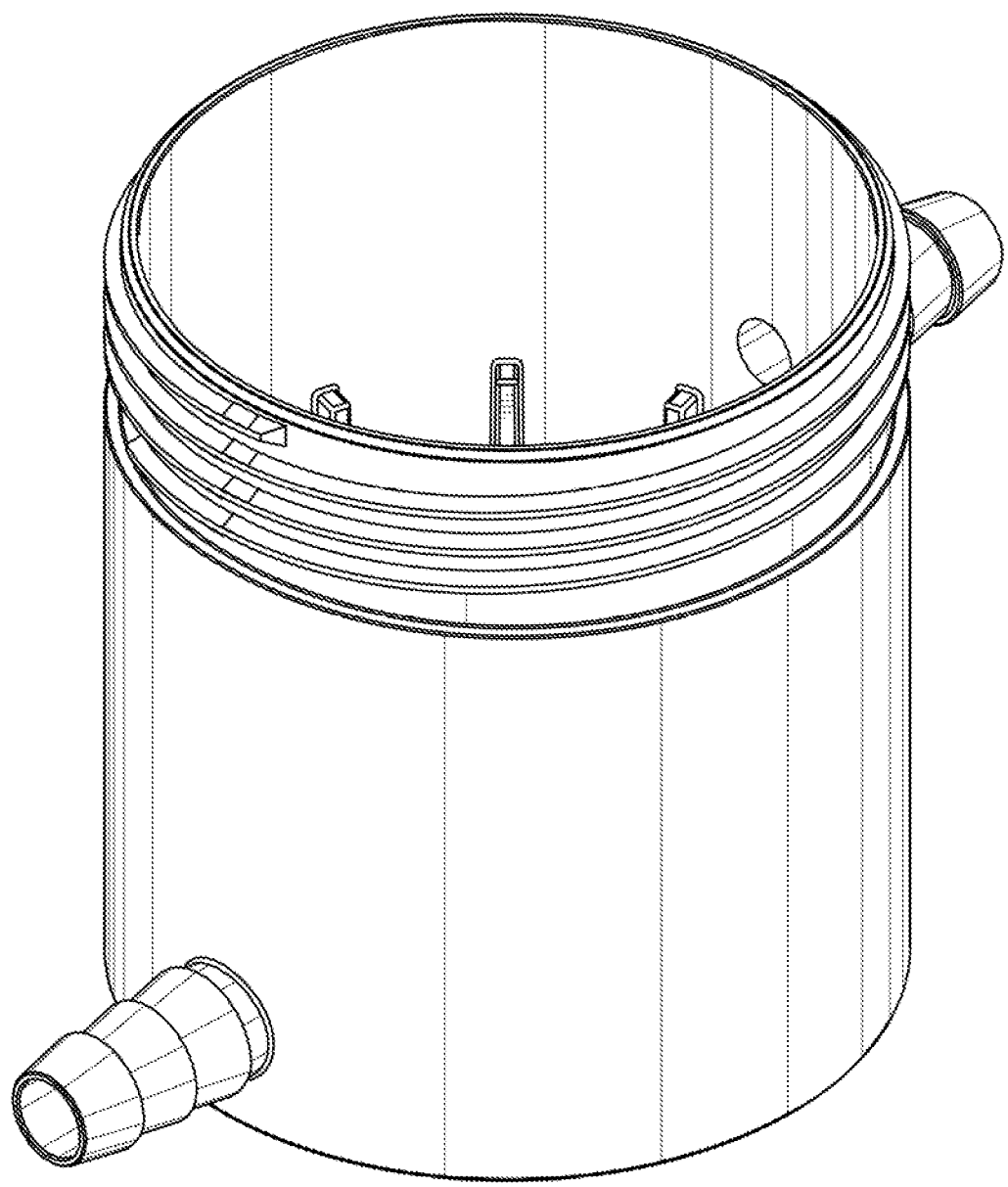
FIG. 13 is a top, left, front perspective view of jar 420.
Figure 14:
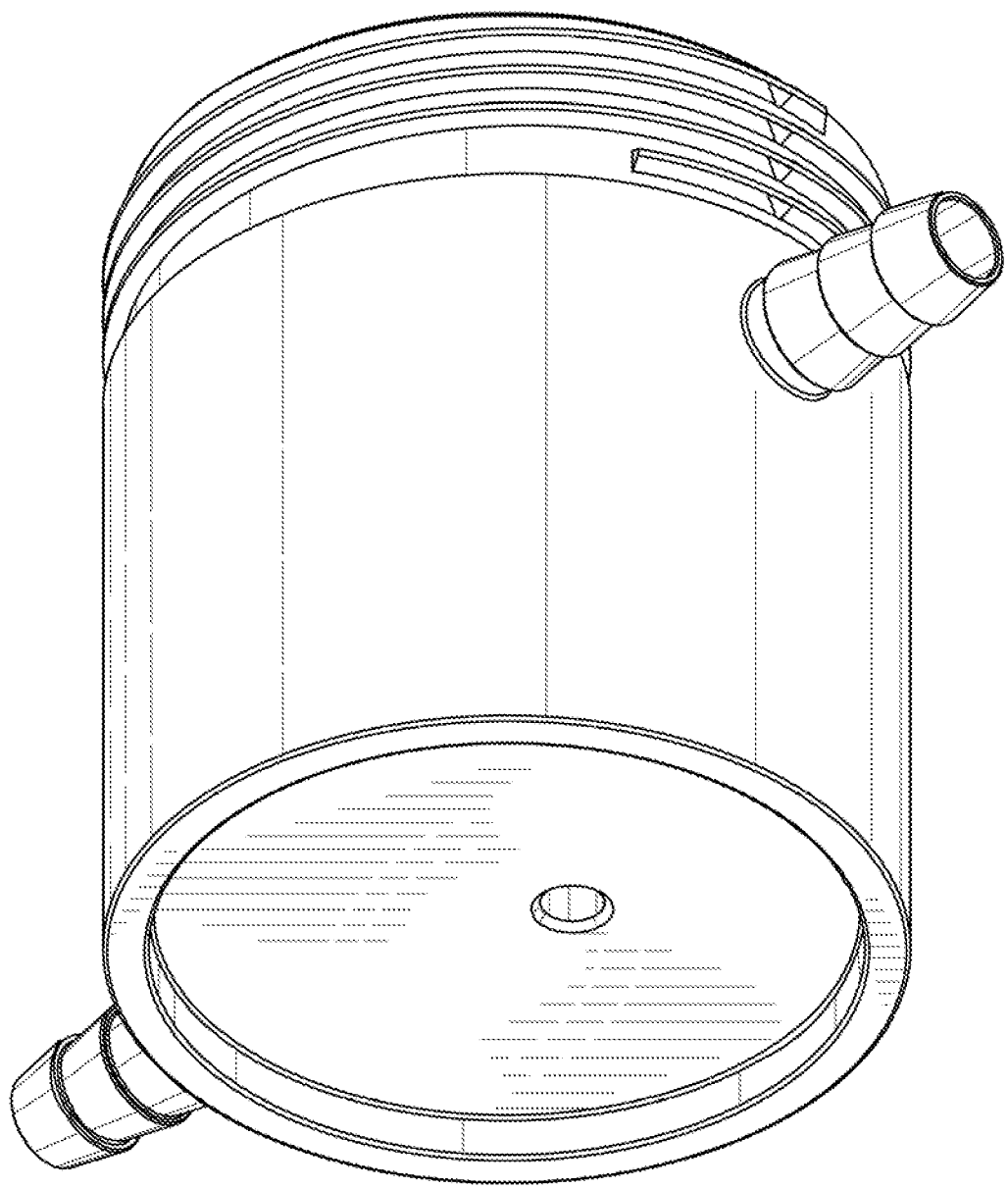
FIG. 14 is a bottom, right, front perspective view of jar 420.
Figure 15:
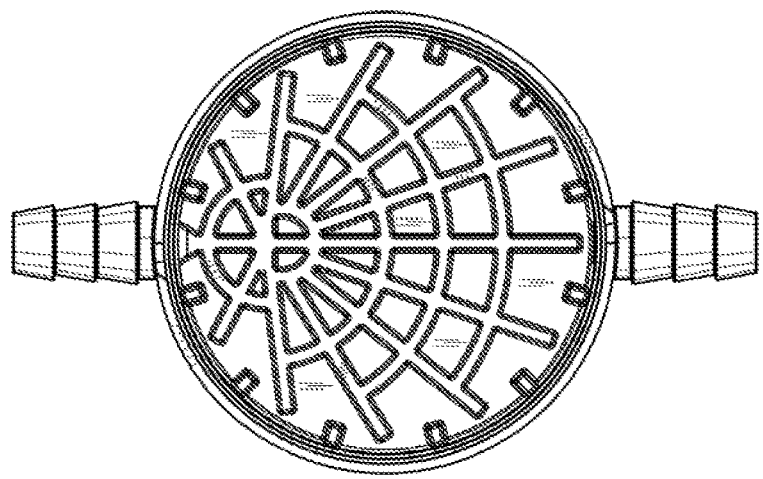
FIG. 15 is a top plan view of jar 420.
Figure 16:
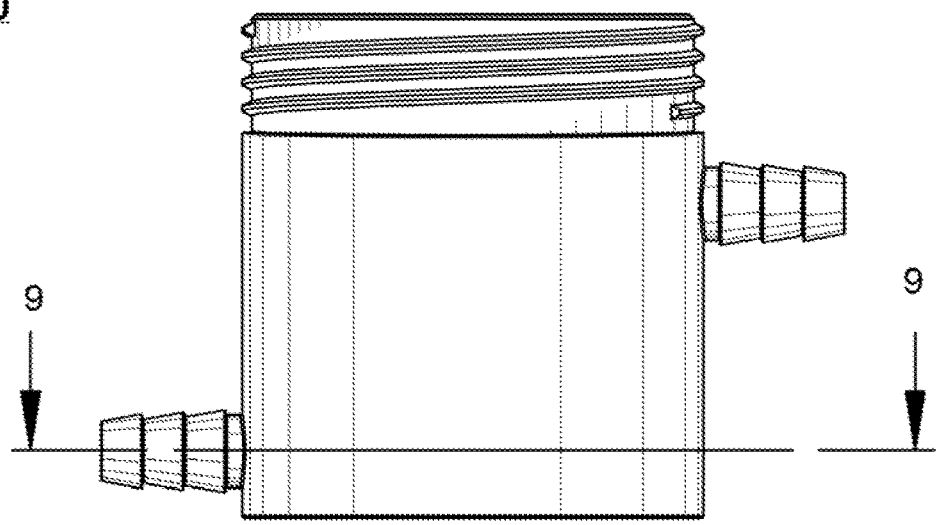
FIG. 16 is a front view of jar 420.
Figure 17:
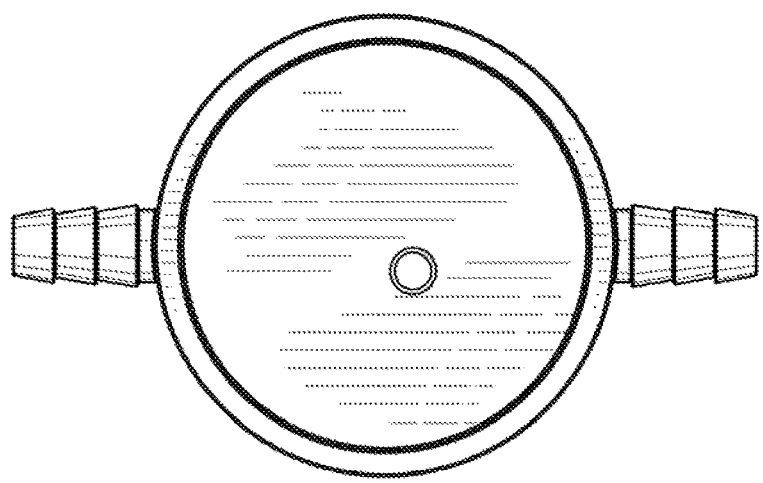
FIG. 17 is a bottom plan view of jar 420.
Figure 20:
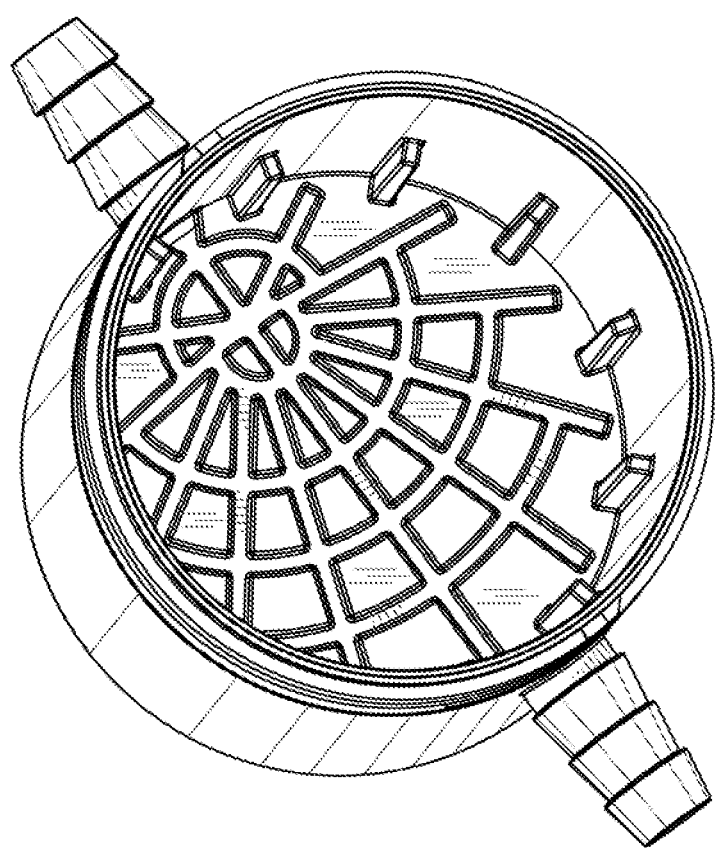
FIG. 20 is a top and front perspective view of jar 420.
Figure 21:
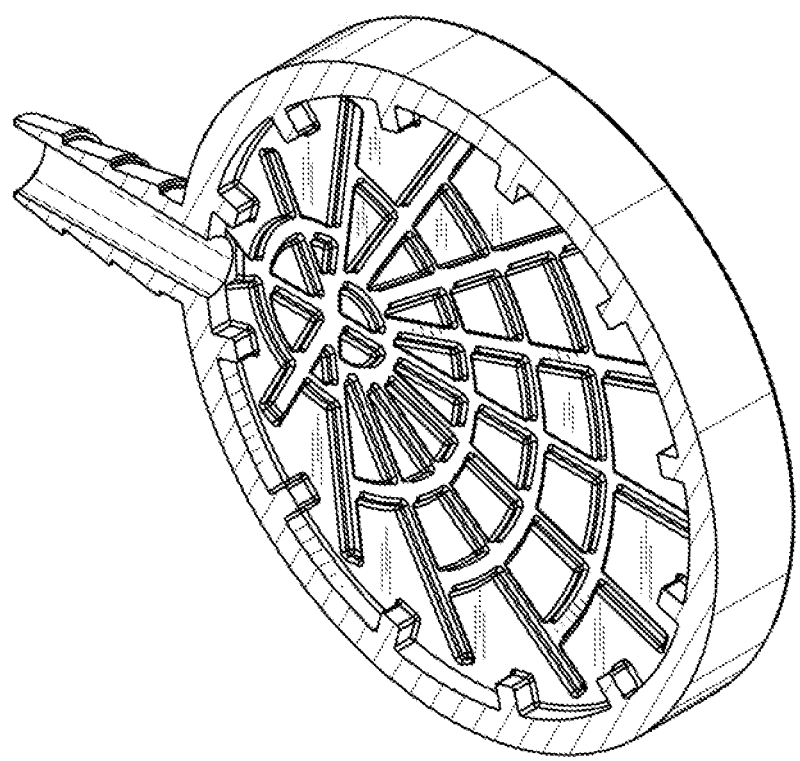
FIG. 21 is a top, right, rear perspective view of a cross section of jar 420 taken as indicated in FIG. 4.
Figure 22:
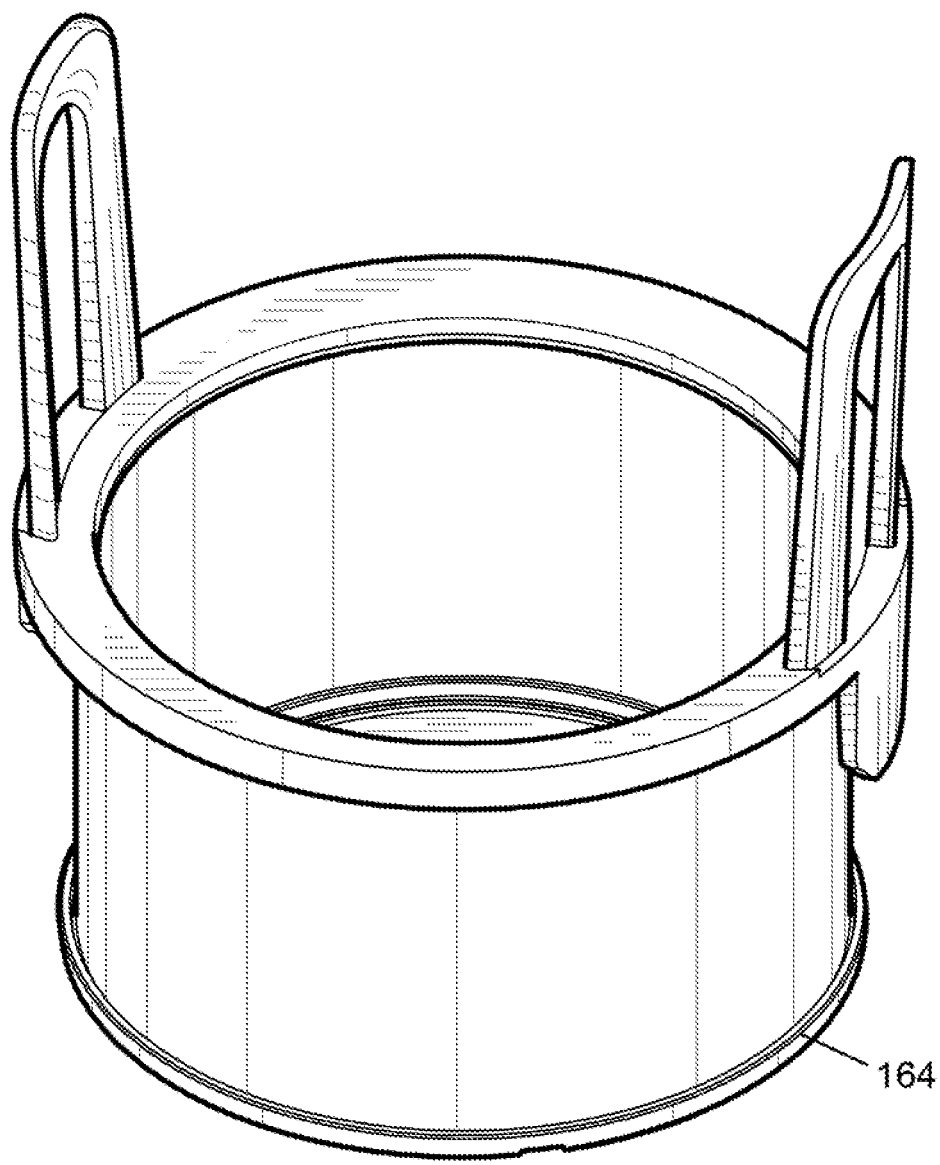
FIG. 22 is a top, front perspective view of basket 454.
Figure 23:
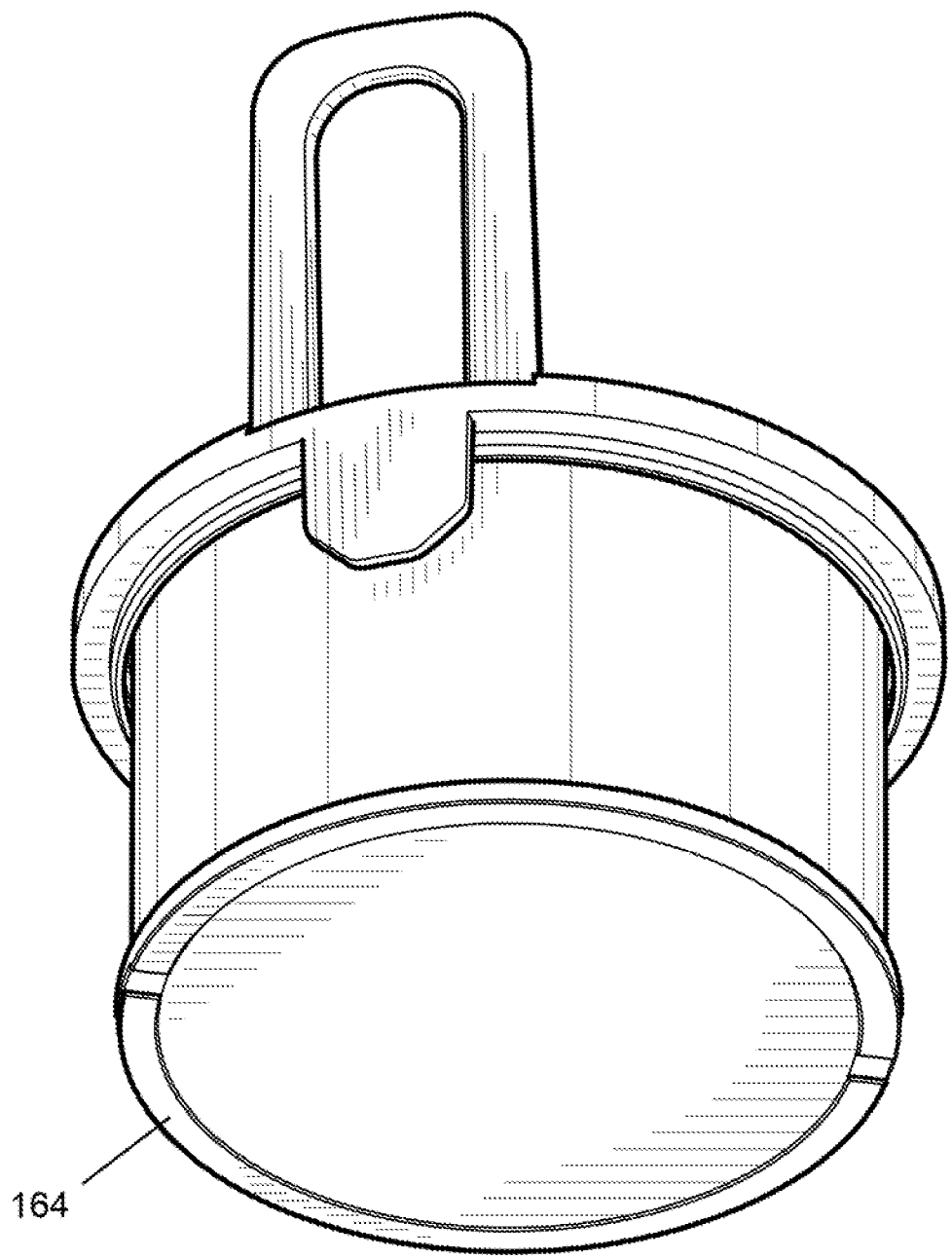
FIG. 23 is a bottom, right perspective view of basket 454.
Figure 24:
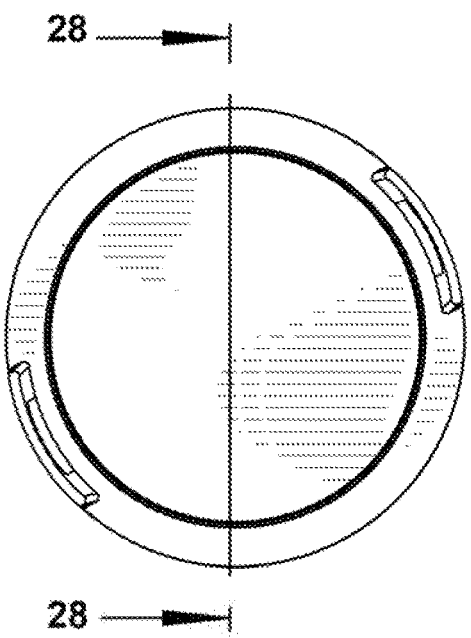
FIG. 24 is a top plan view of basket 454.
Figure 27:
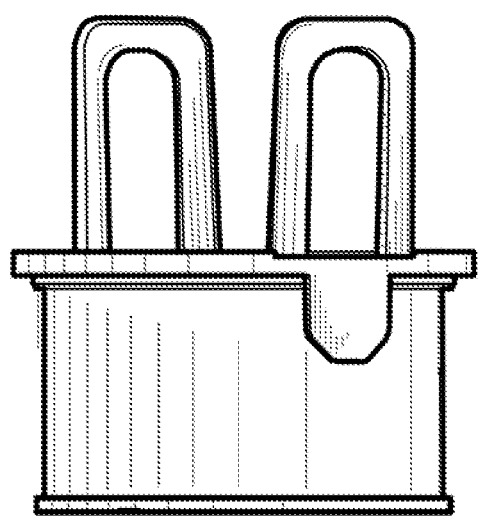
FIG. 27 is a right, front perspective view of basket 454.
Figure 28:
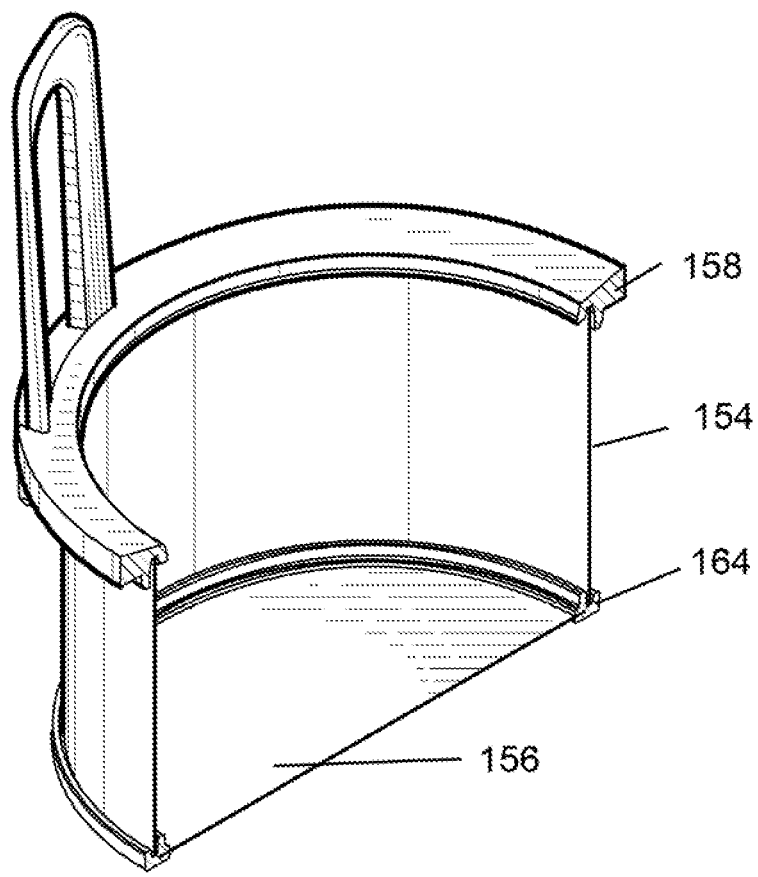
FIG. 28 is a top perspective view of the interior of the cross section of FIG. 24.
Figure 29:
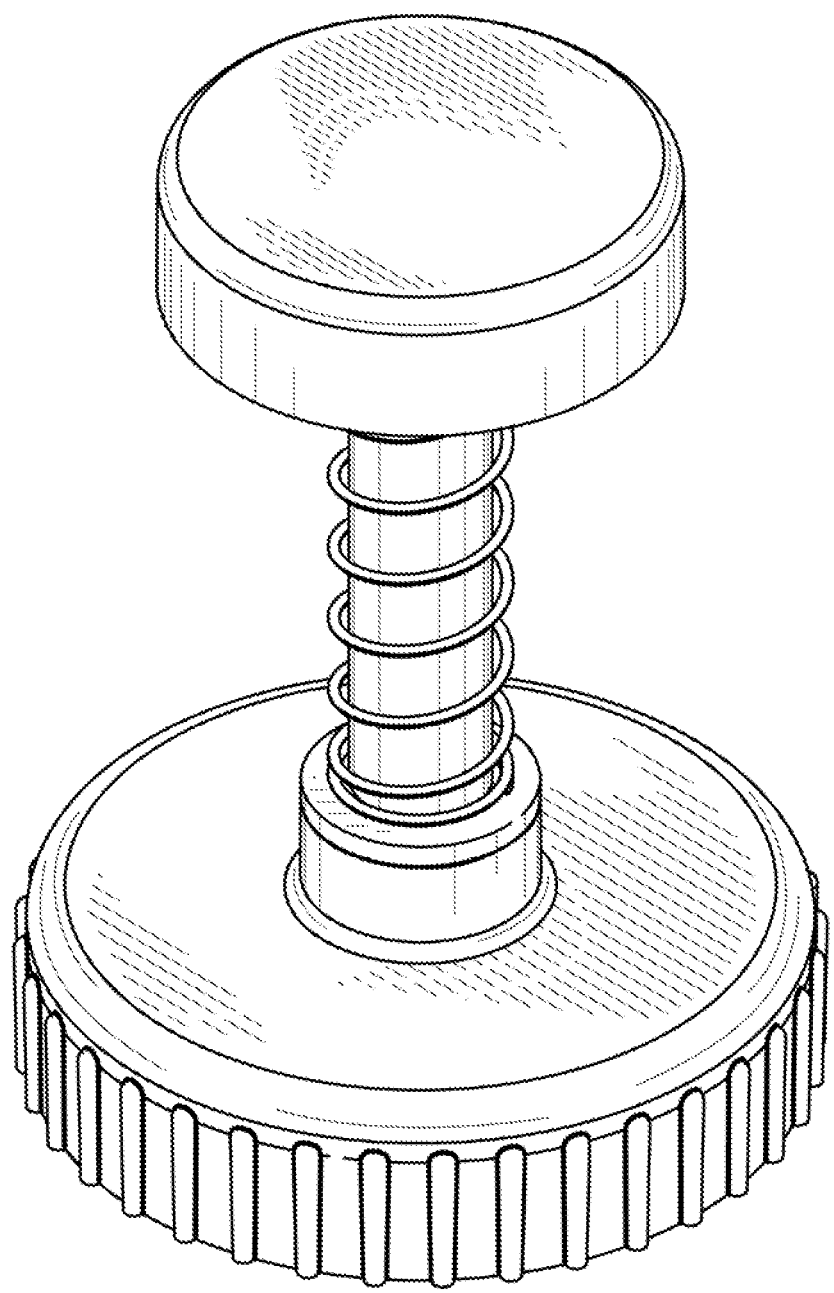
FIG. 29 top perspective view of plunger & cap assembly 480.
Figure 30:
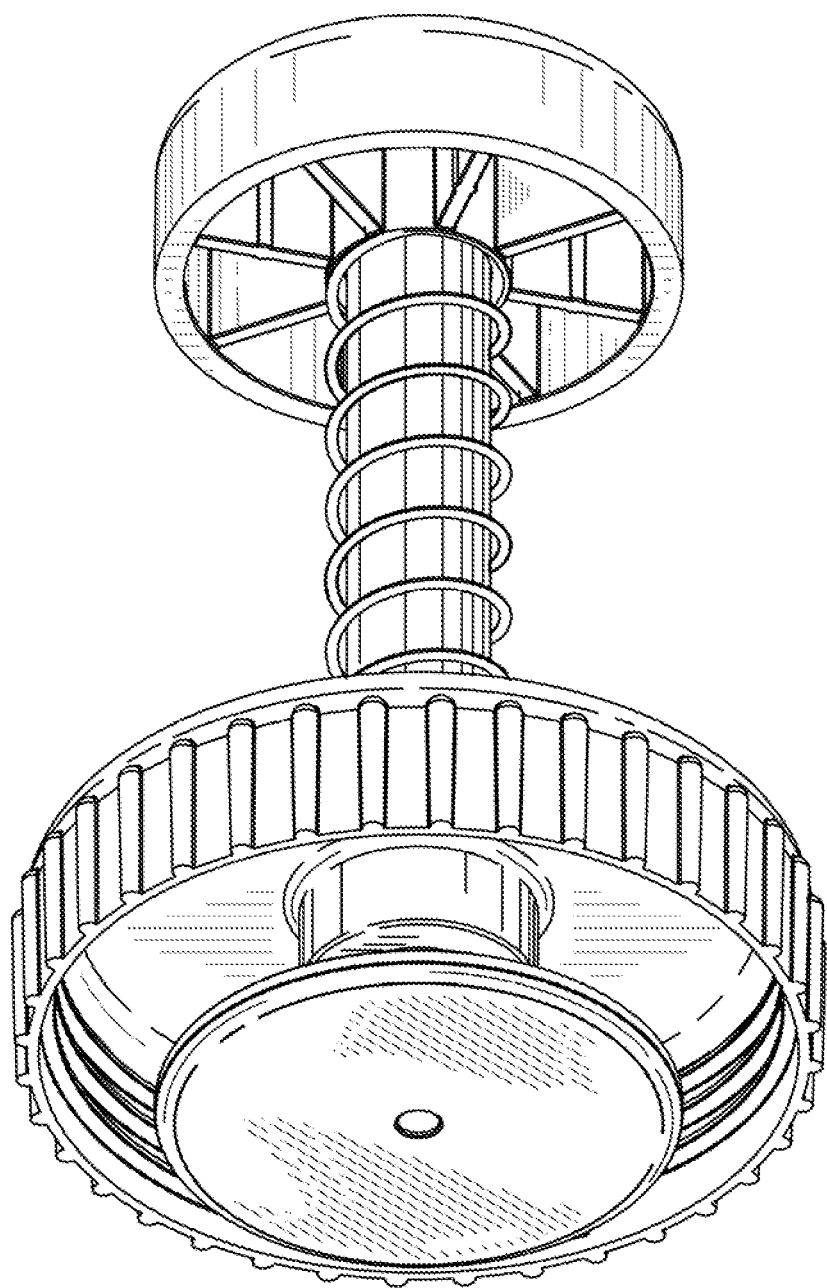
FIG. 30 bottom perspective view of plunger & cap assembly 480.
Figure 31:
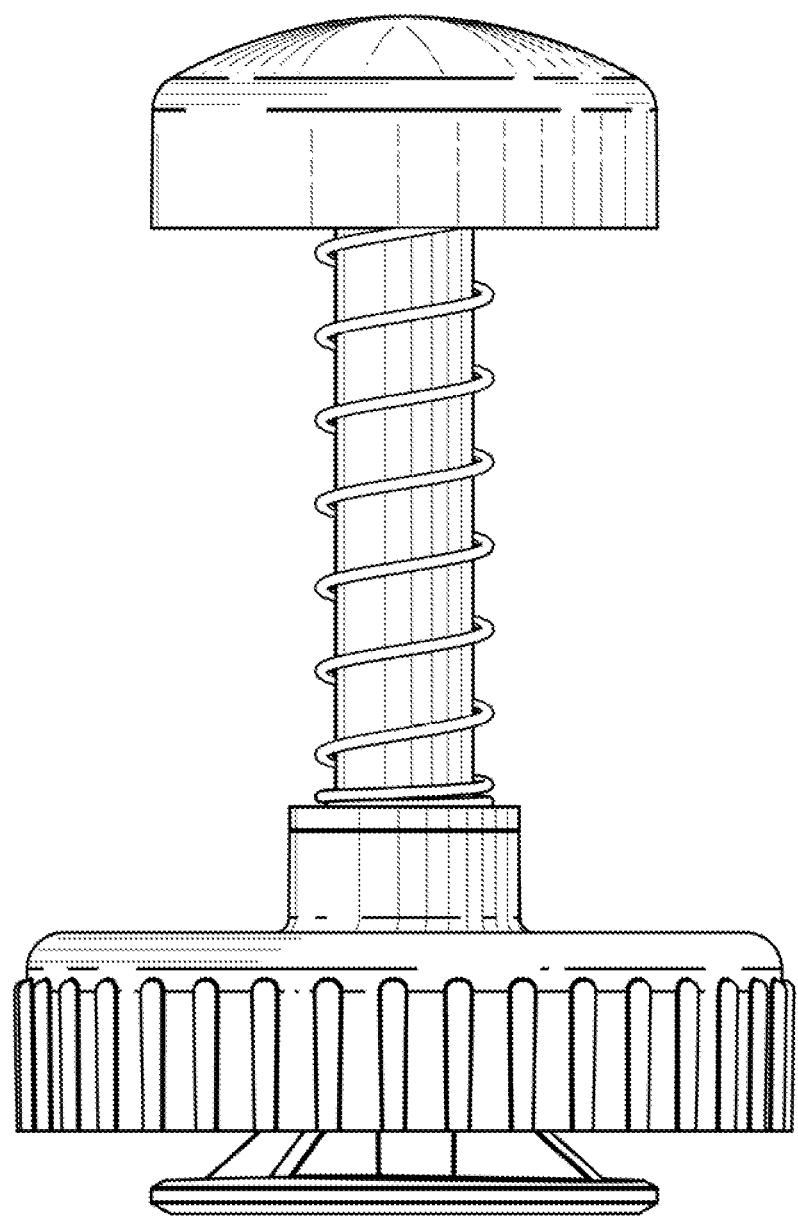
FIG. 31 is a side view of plunger & cap assembly 480.
Figure 32:
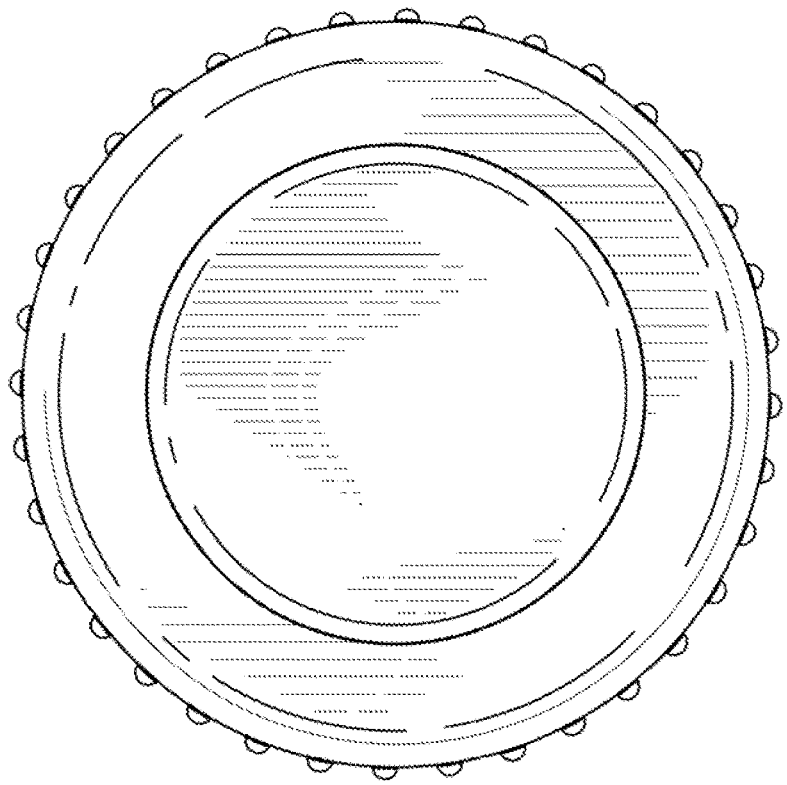
FIG. 32 is a top plan view of plunger & cap assembly 480.
Figure 33:
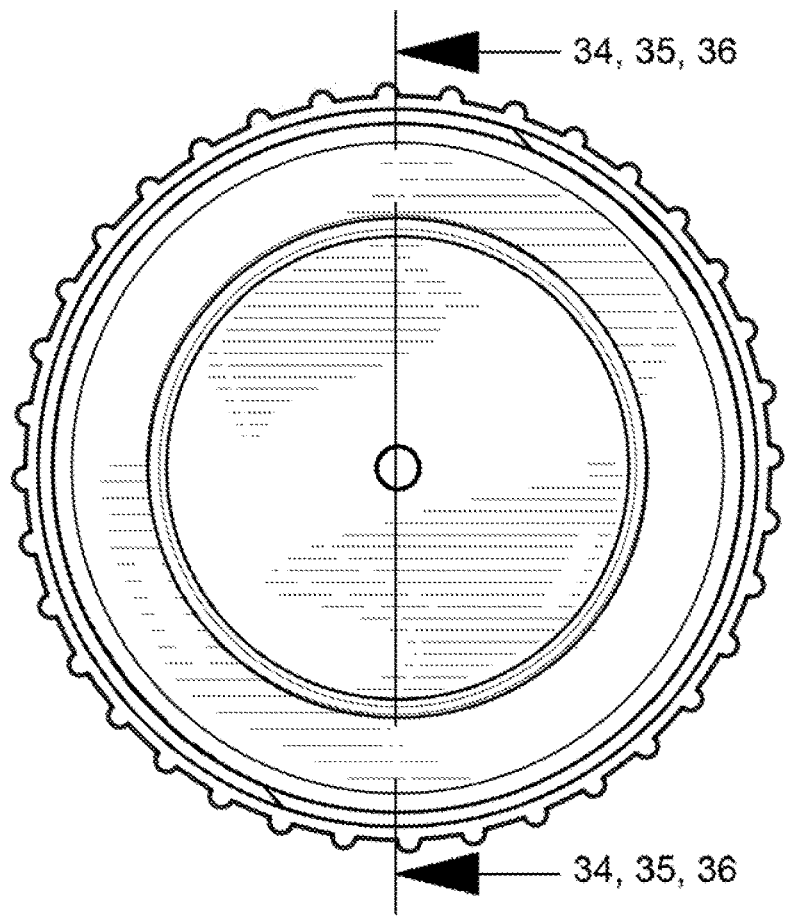
FIG. 33 is a bottom plan view of plunger & cap assembly 480.
Figure 34:
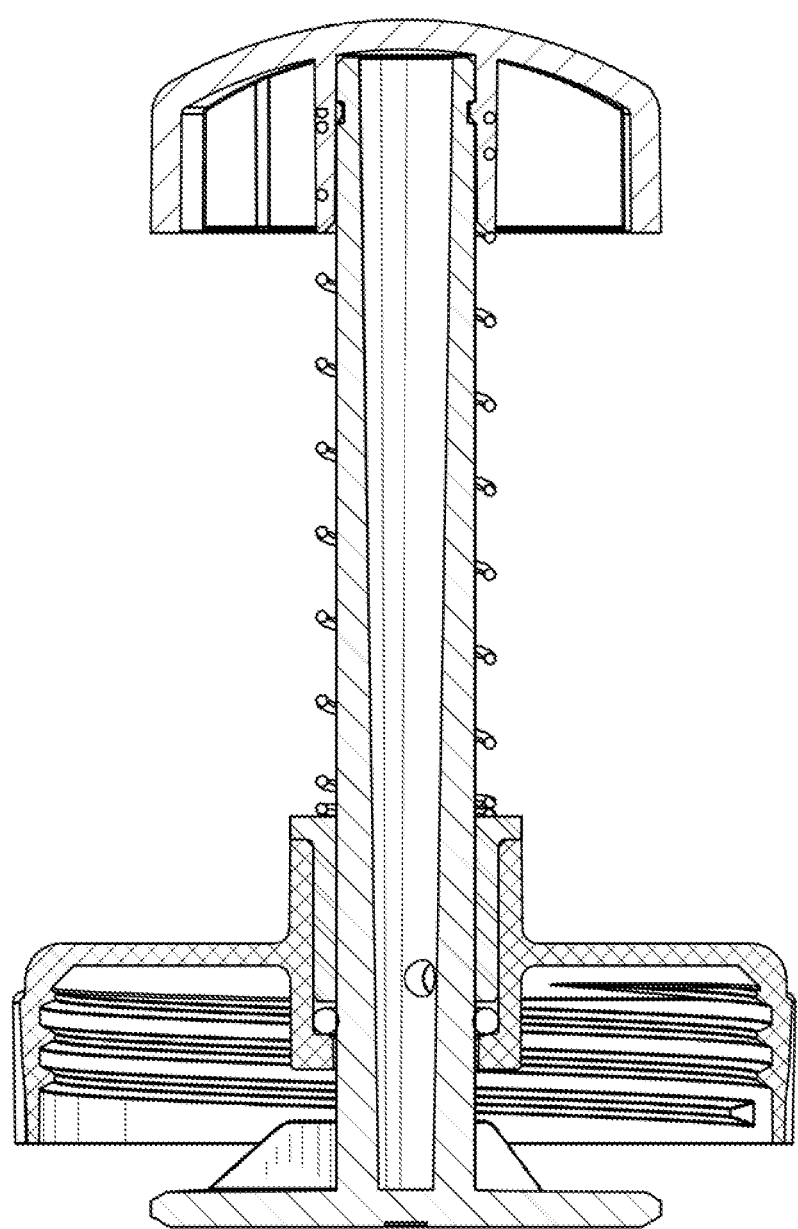
FIG. 34 is a side view of a cross section of FIG. 33.
Figure 35:
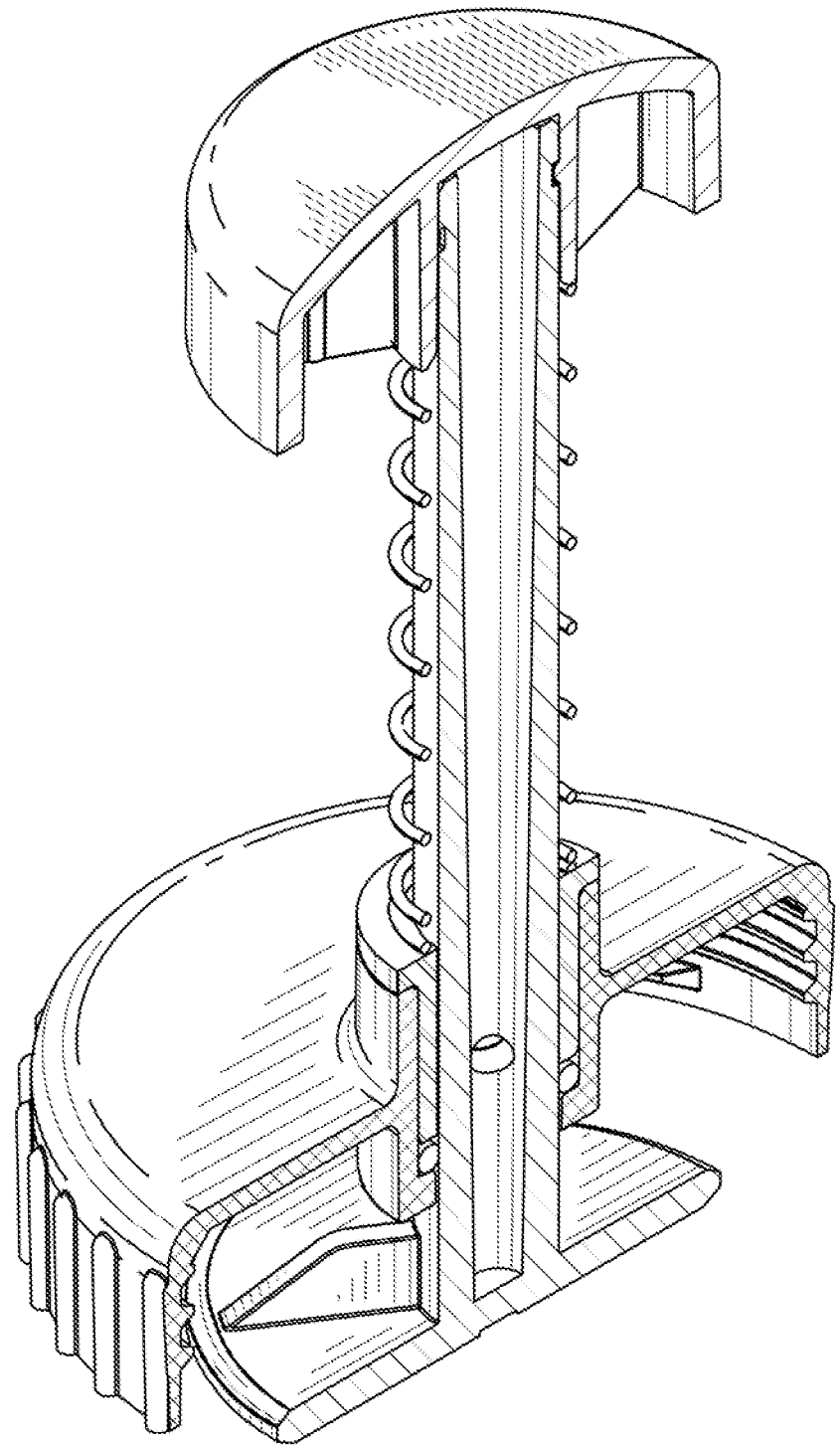
FIG. 35 is a top, side perspective view of a cross section of FIG. 33.
Figure 36:
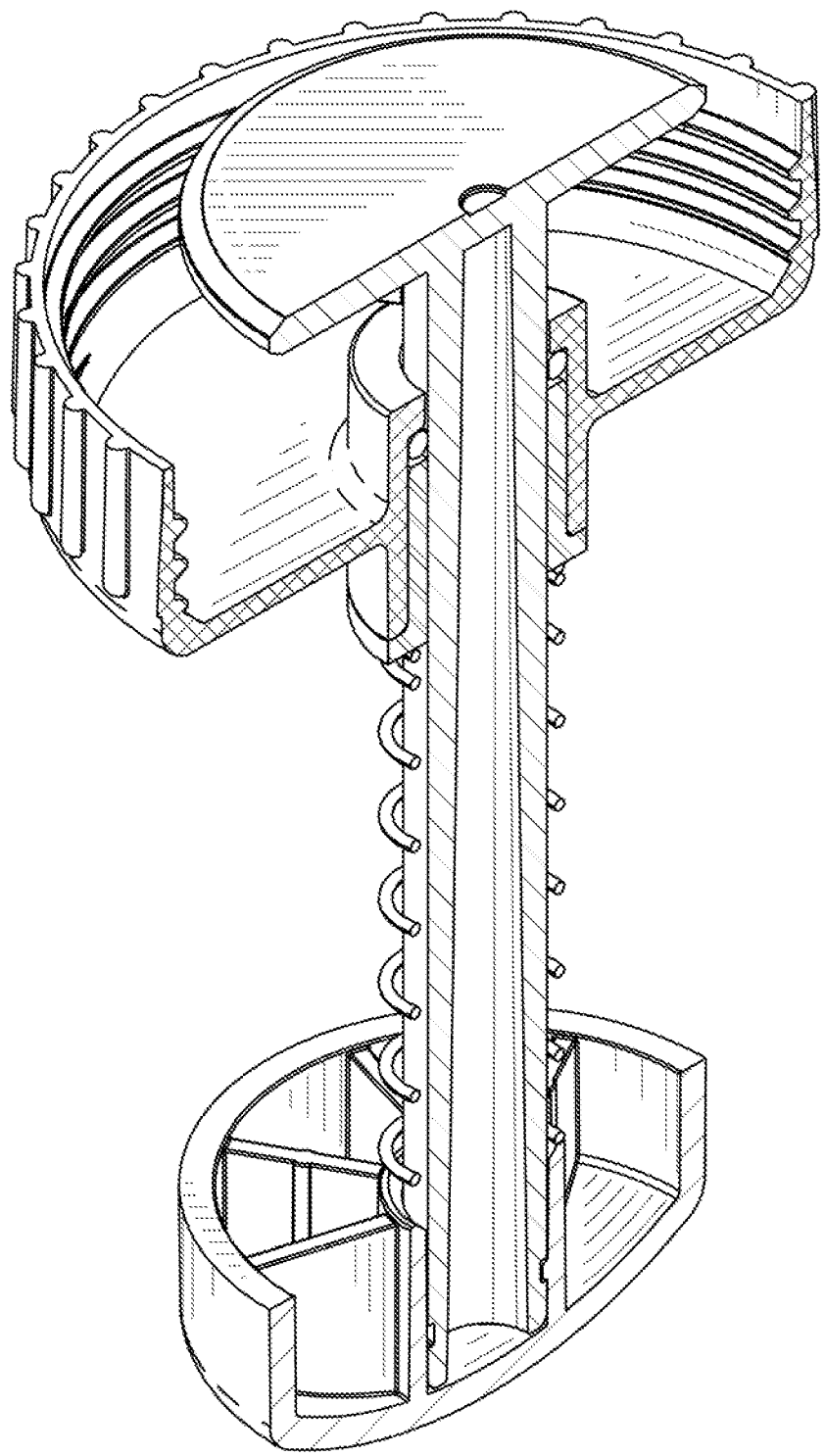
FIG. 36 is a top, side perspective view of a cross section of FIG. 33.

FIG. 13 is a top, left, front perspective view of jar 420.
FIG. 14 is a bottom, right, front perspective view of jar 420.
FIG. 15 is a top plan view of jar 420.
FIG. 16 is a front view of jar 420.
FIG. 17 is a bottom plan view of jar 420.
FIG. 18 is a left side view of jar 420.
FIG. 19 is a right side view of jar 420.
FIG. 20 is a top and front perspective view of jar 420.
FIG. 21 is a top, right, rear perspective view of a cross section of jar 420 taken as indicated in FIG. 4.
FIG. 22 is a top, front perspective view of basket 454.
FIG. 23 is a bottom, right perspective view of basket 454.
FIG. 24 is a top plan view of basket 454.
FIG. 25 is a front, left perspective view of basket 454.
FIG. 26 is a bottom plan view of basket 454.
FIG. 27 is a right, front perspective view of basket 454.
FIG. 28 is a top perspective view of the interior of the cross section of FIG. 24.
FIG. 29 top perspective view of plunger & cap assembly 480.
FIG. 30 bottom perspective view of plunger & cap assembly 480.
FIG. 31 is a side view of plunger & cap assembly 480.
FIG. 32 is a top plan view of plunger & cap assembly 480.
FIG. 33 is a bottom plan view of plunger & cap assembly 480.
FIG. 34 is a side view of a cross section of FIG. 33.
FIG. 35 is a top, side perspective view of a cross section of FIG. 33.
FIG. 36 is a top, side perspective view of a cross section of FIG. 33.

Kits.

The surgical collection assembly 100 with jar 120 and plunger & cap assembly 200 may be delivered in a kit with a piece of suction tubing fixed to the inlet port. Delivery of suction tubing ensures use of clean suction tubing between the collection site and the inlet of the jar 120 so that the collected material is free from other debris that may have been created and removed by other suction tubing. This can be important when the material collected, such as bone, is going to be used for a specific purpose. Providing tubing with the jar 120 ensures that tubing of suitable flexibility is provided to ensure for easier maneuvering of the end of the suction tubing. Finally, delivering the jar 120 with tubing affixed to the inlet removes one source of error for setting up the surgical collection assembly.

The kit may contain two or more baskets. The kit may include an alternative cap 304 in addition to a plunger & cap assembly 200.

Non-Circular Jar.

Note that while the examples provided in this disclosure had a jar with a circular cross section, one of skill in the art will appreciate that a jar with another cross section could be used. For example, the cross section could be oval or egg shaped. Alternative cross sections may be used as long as the design had an engagement between the plunger assembly (or specimen collection lid) and the jar that worked appropriately. Most likely this would be something other than a threaded engagement with the jar. The basket assembly would need to be sized appropriately but would not have to have the exact cross section shape of the jar.

Alternative Baskets.

While the taught the use of baskets with liquid permeable bottoms and liquid permeable sides, those of skill in the art will recognize that for certain applications the bottom may be liquid permeable while the sidewalls are not. This may be appropriate when the collection basket has a very large bottom surface or when the collection process is not intended to collect so much filtered material that the filtered material would get deep. Such a basket may seem more like a relatively flat pan than an elongated cylinder Alternatively, a basket might have a bottom that is not permeable to liquid and rely on the fluids to be pulled out the liquid permeable sidewalls. In such a basket, the basket bottom may be small so that as layers of collected materials pile up, the materials are partially dried by the removal of fluids through nearby sidewalls. Such a basket may seem more like an elongated cylinder than a relatively flat pan.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

What is claimed is:

1. A collection subassembly comprising a collection basket and a collection jar for collecting non-liquid material from a mixture of liquid and non-liquid material obtained during surgery;

the collection basket having:
at least one basket sidewall that forms a perimeter between a basket bottom and a rigid upper portion of the collection basket;
the at least one basket sidewall and the basket bottom forming a container with an open top end;
a permeable portion of the collection basket being liquid permeable; and
the collection basket sized relative to the collection jar so that a gap exists between the collection basket and the collection jar; and
the gap fluidly connected to a jar outlet;

the collection jar comprising:
a walled perimeter of the collection jar joined to a bottom surface of the collection jar;
the walled perimeter of the collection jar defining an open end that may be reversibly sealed with a jar top;
a jar inlet located on the walled perimeter;
the jar outlet located on the walled perimeter; and
the jar inlet located closer to the open end than the jar outlet;
the collection subassembly adapted to respond to suction applied to the jar outlet while a jar top is sealing the collection jar to pull liquid and non-liquid material through a section of tubing connected to the jar inlet of the collection jar;

the mixture of liquid and non-liquid material passing into the collection basket with much of the liquid leaving the collection basket through the permeable portion of the collection basket to enter the gap between the collection basket and the collection jar and then out the jar outlet leaving collected non-liquid material in the collection basket; and the collection subassembly adapted to allow removal of the jar top from the collection jar and then removal of the collection basket from the collection jar to retrieve the collected non-liquid material from the collection basket:
without disconnecting a suction line from the jar outlet; and
without disconnecting the section of tubing from the jar inlet.

2. The collection subassembly of claim 1 wherein the collection basket has at least one basket sidewall and the basket bottom that form a substantially cylindrical container which fits inside the collection jar which is substantially cylindrical.

3. The collection subassembly of claim 1 wherein the at least one basket sidewall is sufficiently flexible to allow the at least one basket sidewall of the collection basket to be passed through the rigid upper portion of the collection basket to at least partially invert the collection basket and facilitate removal of the collected non-liquid material.

4. The collection subassembly of claim 1 wherein:
the collection basket has a protrusion extending above the at least one basket sidewall to provide a location for grasping the collection basket to move the collection basket into the collection jar; and
the collection jar is adapted to prohibit placement of the collection basket into the collection jar in an orientation that would allow the protrusion to obstruct a flow of liquid and non-liquid material from the jar inlet to the collection basket.

5. The collection subassembly of claim 4 wherein:
the protrusion is a handle with an open area within a perimeter of the handle and the collection jar is adapted to allow placement of the collection basket into the collection jar in an orientation that allows a flow of liquid and non-liquid material to flow from the jar inlet through the open area within the perimeter of the handle and into the collection basket.

6. The collection subassembly of claim 1 wherein at least a portion of the at least one basket sidewall is liquid permeable.

7. The collection subassembly of claim 1 wherein at least a portion of the basket bottom is liquid permeable.

8. The collection subassembly of claim 1 wherein the bottom surface of the collection jar has a pattern of recessed paths that are fluidly connected to the jar outlet.

9. The collection subassembly of claim 1 wherein the collection basket is maintained in a substantially cylindrical shape by a lower basket ring which maintains the basket bottom in a substantially flat orientation inside an inside perimeter of the lower basket ring.

10. The collection subassembly of claim 9 wherein the lower basket ring can be moved to proximity of the rigid upper portion of the collection basket as the at least one basket sidewall of the collection basket are passed through the rigid upper portion of the collection basket to at least partially invert the collection basket and facilitate removal of the collected non-liquid material.

11. The collection subassembly of claim 1 wherein the jar inlet and the jar outlet are on opposite sides of the walled perimeter of the collection jar.

12. The collection subassembly of claim 1 wherein the jar inlet and the jar outlet are not on opposite sides of the walled perimeter of the collection jar.

13. The collection subassembly of claim 1 further comprising a lid to reversibly close the collection jar.

14. The collection subassembly of claim 1 further comprising a lid and plunger subassembly to reversibly close the collection jar and to allow collected non-liquid material in the collection basket to be compressed by a plunger that moves downward from the lid and plunger subassembly while staying within the container formed by the at least one basket sidewall and the basket bottom.

15. The collection subassembly of claim 14 wherein the lid and plunger subassembly includes a spring to apply pressure to the plunger to move the plunger to a raised position which does not impede the mixture of liquid and non-liquid material from moving from the jar inlet into the collection basket.

16. The collection subassembly of claim 14 wherein the plunger moves downward from the lid and plunger subassembly while staying within the container formed by the at least one basket sidewall and the basket bottom to provide a compression of the non-liquid material between the plunger and the basket bottom as the basket bottom is at least partially supported by the bottom surface of the collection jar.

17. The collection subassembly of claim 16 wherein the compression of the non-liquid material between the plunger and the basket bottom:
1) occurs as the basket bottom is at least partially supported by the bottom surface of the collection jar; and
2) allows liquid material to pass through the basket bottom and through a pattern of recessed paths in the bottom surface of the collection jar to the jar outlet.

18. The collection subassembly of claim 1 wherein the walled perimeter of the collection jar has a set of ribs, the set of ribs creating a set of pathways within the walled perimeter to allow liquid to pass through liquid permeable at least one basket sidewall and through the set of pathways to travel to the jar outlet.

19. The collection subassembly of claim 18 wherein the set of ribs supports the rigid upper portion of the collection basket to position the collection basket within the collection jar.

20. The collection subassembly of claim 18 wherein the set of ribs engages with the rigid upper portion of the collection basket to limit allowed orientations of the collection basket within the collection jar relative to the jar inlet.

21. A method for collecting non-liquid material from a mixture of liquid and non-liquid material obtained during surgery the method comprising:
obtaining the collection subassembly of claim 1 for collecting non-liquid material from a mixture of liquid and non-liquid material obtained during surgery;
inserting the collection basket with the permeable portion into the collection jar;
adding a jar top to seal the open end of the collection jar;
such that suction applied to the jar outlet will pull a flow of liquid and non-liquid material through inlet tubing connected to the jar inlet, the flow of liquid and non-liquid material passing through the jar inlet, with at least some fluid in the flow of liquid and non-liquid material passing through the permeable portion of the collection basket and into the gap then to the jar outlet to leave collected material in the collection basket;

connecting the inlet tubing to the jar inlet;

connecting outlet tubing to the jar outlet;

applying suction to the outlet tubing connected to the jar outlet so that whenever a non-jar end of the inlet tubing is placed into a surgical site, liquid and non-liquid materials are pulled through the inlet tubing through the jar inlet and into the collection basket;

removing the non-jar end of the inlet tubing from the surgical site;

removing the jar top from the collection jar;

removing the collection basket with the collected material from the collection jar; and removing collected material from the collection basket.

22. The method of claim 21 wherein removing collected material from the collection basket includes moving the basket bottom of the collection basket through an upper portion of the collection basket to at least partially invert the collection basket.

23. The method of claim 21 wherein the collection subassembly of claim 1 further comprises a lid and plunger subassembly to reversibly close the collection jar and to allow collected non-liquid material in the collection basket to be compressed by a plunger that moves downward from the lid and plunger subassembly while staying within the container formed by the at least one basket sidewall and the basket bottom; and wherein before removing the jar top from the collection jar to remove collected material, the plunger moves downward from the lid and plunger subassembly while staying within the container formed by the at least one basket sidewall and the basket bottom to compress the collected material.

24. The method of claim 23 wherein the plunger compresses non-liquid material between the plunger and the basket bottom as the basket bottom is at least partially supported by the bottom surface of the collection jar.

25. The method of claim 21 wherein the collection subassembly of claim 1 further comprises a lid and plunger subassembly to reversibly close the collection jar and to allow collected non-liquid material in the collection basket to be compressed by a plunger that moves downward from the lid and plunger subassembly while staying within the container formed by the at least one basket sidewall and the basket bottom; and wherein before removing the jar top from the collection jar to remove collected material, the plunger moves downward from the lid and plunger subassembly while staying within the container formed by the at least one basket sidewall and the basket bottom to assist the suction in removing liquid from the collected material.

26. The method of claim 21 wherein the at least one basket sidewall is sufficiently flexible to allow the at least one basket sidewall of the collection basket to be passed through the rigid upper portion of the collection basket to at least partially invert the collection basket and facilitate removal of the collected non-liquid material; and removing collected non-liquid material from the collection basket includes at least partially inverting the collection basket.

27. The method of claim 21 wherein the collection basket has a protrusion extending above the at least one basket sidewall to provide a location for grasping the collection basket to move the collection basket into the collection jar; and the collection jar is adapted to prohibit placement of the collection basket into the collection jar in a blocking orientation that would allow the protrusion to obstruct the flow of liquid and non-liquid material from the jar inlet to the collection basket; and inserting the collection basket with the permeable portion into the collection jar includes selecting a non-blocking orientation of the collection basket within the collection jar that is not prohibited by an interaction of the collection jar with the collection basket.

\* \* \* \* \*

UNITED STATES PATENT AND TRADEMARK OFFICE
CERTIFICATE OF CORRECTION

PATENT NO. : 10,940,247 B2
APPLICATION NO. : 16/248703
DATED : March 9, 2021
INVENTOR(S) : Gretchen Willard et al.

Page 1 of 1

It is certified that error appears in the above-identified patent and that said Letters Patent is hereby corrected as shown below:

In the Claims

Column 10, Lines 56, 61 and 62, Claim 1 "ajar", each of the three occurrences, should read --a jar--.
Column 12, Line 62, Claim 21 "ajar" should read --a jar--.

Signed and Sealed this
Sixth Day of July, 2021

Drew Hirshfeld
*Performing the Functions and Duties of the
Under Secretary of Commerce for Intellectual Property and
Director of the United States Patent and Trademark Office*